(12) United States Patent
Katz et al.

(10) Patent No.: US 10,561,784 B2
(45) Date of Patent: Feb. 18, 2020

(54) STATIONARY OPTICAL MONITORING SYSTEM FOR BLOOD PROCESSING SYSTEM

(71) Applicant: Fenwal, Inc., Lake Zurich, IL (US)

(72) Inventors: Steven R. Katz, Deerfield, IL (US); Jeffrey Maher, Lake Barrington, IL (US); Eric Linner, Crystal Lake, IL (US); Ryan DeLacey, Wheaton, IL (US); Robert Crampton, Gurnee, IL (US); Richard L. West, Lake Villa, IL (US); Brian C. Case, Lake Villa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 478 days.

(21) Appl. No.: 15/609,382

(22) Filed: May 31, 2017

(65) Prior Publication Data

US 2018/0344920 A1    Dec. 6, 2018

(51) Int. Cl.
*A61M 1/36* (2006.01)

(52) U.S. Cl.
CPC ........ *A61M 1/3693* (2013.01); *A61M 1/3607* (2014.02); *A61M 2205/12* (2013.01); *A61M 2205/14* (2013.01); *A61M 2205/3306* (2013.01)

(58) Field of Classification Search
CPC .............. A61M 1/3693; A61M 1/3695; A61M 1/3696; A61M 1/3698; A61M 1/3607; A61M 2205/12; A61M 2205/14; A61M 2205/3306; G01N 15/1636; G01N 33/49; G01N 15/05

See application file for complete search history.

(56) References Cited

U.S. PATENT DOCUMENTS

| | | | |
|---|---|---|---|
| 3,727,066 A | 4/1973 | Louderback et al. |
| 3,752,995 A | 8/1973 | Leidholz |
| 3,778,171 A | 12/1973 | Chervenka |
| 4,120,449 A | 10/1978 | Brown et al. |
| 4,409,820 A | 10/1983 | Nash |

(Continued)

FOREIGN PATENT DOCUMENTS

| | | |
|---|---|---|
| EP | 0 342 730 A2 | 11/1989 |
| EP | 0 771 569 A2 | 5/1997 |

(Continued)

*Primary Examiner* — Philip R Wiest
(74) *Attorney, Agent, or Firm* — Cook Alex Ltd.

(57) ABSTRACT

A blood processing system includes a centrifuge and an optical monitoring system mounted at a stationary radial position with respect to the centrifuge. A flow circuit may be mounted within the centrifuge, with an umbilicus of the flow circuit extending outside of the centrifuge. A midsection of the umbilicus is orbited around a rotational axis of the centrifuge at a uniform first speed, which causes the centrifuge to rotate at a non-uniform second speed that is approximately double the first speed. The monitoring system is configured to view the flow circuit through a radial window of the centrifuge to determine a characteristic of the flow circuit. The yoke and/or umbilicus may occasionally move into position between the monitoring system and the window, so a controller of the monitoring system is configured to determine when unobstructed light reflected through the window by the centrifuge is received by the monitoring system.

20 Claims, 13 Drawing Sheets

(56) References Cited

U.S. PATENT DOCUMENTS

| | | |
|---|---|---|
| 4,468,219 A | 8/1984 | George et al. |
| 4,557,719 A | 12/1985 | Neumann et al. |
| 4,604,086 A | 8/1986 | Benko et al. |
| 4,810,090 A | 3/1989 | Boucher et al. |
| 5,104,526 A | 4/1992 | Brown et al. |
| 5,260,598 A | 11/1993 | Brass et al. |
| 5,298,476 A | 3/1994 | Hotta |
| 5,316,666 A | 5/1994 | Brown et al. |
| 5,316,667 A | 5/1994 | Brown et al. |
| 5,400,261 A | 3/1995 | Reynolds |
| 5,437,598 A | 8/1995 | Antwiler |
| 5,570,697 A | 11/1996 | Walker et al. |
| 5,573,678 A | 11/1996 | Brown et al. |
| 5,592,402 A | 1/1997 | Beebe et al. |
| 5,605,842 A | 2/1997 | Langley et al. |
| 5,611,997 A | 3/1997 | Langley et al. |
| 5,628,915 A | 5/1997 | Brown et al. |
| 5,632,893 A | 5/1997 | Brown et al. |
| 5,639,382 A | 6/1997 | Brown |
| 5,656,163 A | 8/1997 | Brown |
| 5,868,696 A | 2/1999 | Giesler et al. |
| 5,948,271 A | 9/1999 | Wardwell et al. |
| 5,958,250 A | 9/1999 | Brown et al. |
| 5,961,842 A | 10/1999 | Min et al. |
| 5,980,757 A | 11/1999 | Brown et al. |
| 5,980,760 A | 11/1999 | Min et al. |
| 6,063,292 A | 5/2000 | Leung |
| 6,254,784 B1 | 7/2001 | Nayak et al. |
| 6,312,607 B1 | 11/2001 | Brown et al. |
| 6,899,666 B2 | 5/2005 | Brown |
| 7,327,443 B2 | 2/2008 | Scibona et al. |
| 7,355,685 B2 | 4/2008 | Scibona et al. |
| 7,422,693 B2 | 9/2008 | Carter et al. |
| 7,605,388 B2 | 10/2009 | Carter et al. |
| 7,951,059 B2 | 5/2011 | Sweat |
| 9,594,020 B2 * | 3/2017 | Koudelka .......... A61M 1/3693 |
| 2004/0133086 A1 | 7/2004 | Ciurczak |
| 2004/0151633 A1 | 8/2004 | De Gaulle et al. |
| 2007/0239033 A1 | 10/2007 | Tearney |
| 2008/0014181 A1 | 1/2008 | Ariff et al. |
| 2008/0041772 A1 | 2/2008 | Sweat et al. |
| 2008/0045394 A1 | 2/2008 | Kolenbrander |
| 2009/0073456 A1 | 3/2009 | Wax |
| 2009/0129976 A1 | 5/2009 | Hoshino |
| 2011/0058070 A1 | 3/2011 | Awazu |
| 2011/0143905 A1 | 6/2011 | Kolenbrander et al. |
| 2012/0190945 A1 | 7/2012 | Yamanaka |
| 2014/0008277 A1 | 1/2014 | Foley |
| 2014/0030729 A1 | 1/2014 | Basiji |
| 2014/0045668 A1 | 2/2014 | Case et al. |

FOREIGN PATENT DOCUMENTS

| | | |
|---|---|---|
| EP | 0 779 077 A1 | 6/1997 |
| WO | WO 96/40319 A1 | 12/1996 |
| WO | WO 03/000026 A2 | 1/2003 |
| WO | WO 03/026724 A1 | 4/2003 |
| WO | WO 2008/021633 A2 | 2/2008 |
| WO | WO 2008/114164 A1 | 9/2008 |

* cited by examiner

STATIONARY OPTICAL MONITORING SYSTEM FOR BLOOD PROCESSING SYSTEM

BACKGROUND

Field of the Disclosure

The disclosure relates to blood treatment systems and methods. More particularly, the disclosure relates to systems and methods for optically detecting a disposable flow circuit mounted within a rotating centrifuge from a stationary location.

Description of Related Art

Various blood processing systems now make it possible to collect particular blood constituents, rather than whole blood, from a blood source. Typically, in such systems, whole blood is drawn from a blood source, the particular blood component or constituent is separated, removed, and collected, and the remaining blood constituents are returned to the blood source. Removing only particular constituents is advantageous when the blood source is a human donor or patient, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents through centrifugation. This requires that the whole blood be passed through a centrifuge after it is withdrawn from, and before it is returned to, the blood source. To avoid contamination and possible infection (if the blood source is a human donor or patient), the blood is preferably contained within a sealed, sterile fluid flow system during the entire centrifugation process. Typical blood processing systems thus include a permanent, reusable assembly containing the hardware (centrifuge, drive system, pumps, valve actuators, programmable controller, and the like) that spins and pumps the blood, and a disposable, sealed, and sterile flow circuit that is mounted in cooperation on the hardware.

The centrifuge engages and spins the disposable flow circuit during a blood separation step. As the flow circuit is spun by the centrifuge, the heavier (greater specific gravity) components of the whole blood in the flow circuit, such as red blood cells, move radially outwardly away from the center of rotation toward the outer or "high-G" wall of the centrifuge. The lighter (lower specific gravity) components, such as plasma, migrate toward the inner or "low-G" wall of the centrifuge. Various ones of these components can be selectively removed from the whole blood by providing appropriately located channeling seals and outlet ports in the flow circuit. For example, in one blood separation procedure, plasma is separated from cellular blood components and collected, with the cellular blood components and a replacement fluid being returned to the blood source.

According to one known design, the centrifuge may be rotated about a rotational axis by an umbilicus. Umbilicus-driven centrifuges have been known since the 1970s, as described in U.S. Pat. No. 4,120,449, which is hereby incorporated herein by reference. In an umbilicus-based system, the centrifuge is connected to a first end of an umbilicus, while the opposite end of the umbilicus is spaced from the first end along the rotational axis of the centrifuge. The first end of the umbilicus is free to twist and rotate with the centrifuge, while the opposite end is held in place without rotating or twisting. A section of the umbilicus between its ends is orbited around the centrifuge by a yoke. The yoke and associated section of the umbilicus orbit around the rotational axis of the centrifuge at a speed that is commonly referred to as "one omega."

Due to one end of the umbilicus being fixed in place, the umbilicus tends to become twisted about its central axis as its central section is orbited about the rotational axis of the centrifuge by the yoke. However, the material composition of the umbilicus is such that it untwists itself, rather than kinking or otherwise becoming inoperative. This has the effect of increasing the rate at which the centrifuge spins, because the free end of the umbilicus (to which it is secured) is the only end of the umbilicus that may untwist to oppose the tendency of the umbilicus to become twisted. The yoke being rotated to orbit the central section of the umbilicus around the rotational axis of the centrifuge at the "one omega" speed combines with the action of the umbilicus to untwist about its own central axis to impart a "two omega" average rotational speed to the bowl and spool of the centrifuge, which is twice the "one omega" rotational speed of the yoke.

The status of fluid being separated in the centrifuge (namely, in the disposable flow circuit mounted within the centrifuge) is monitored by an optical monitoring system. According to one known approach, an optical monitoring system is mounted onto the yoke and, thus, rotates at the "one omega" speed, as described in U.S. Pat. No. 5,316,667, which is hereby incorporated herein by reference. By being associated with the yoke, the field of vision of the optical monitoring system is never interrupted by the umbilicus.

According to an alternative approach, the optical monitoring system may be mounted to a stationary radial location, as described in U.S. Patent No. 2014/0045668, which is hereby incorporated herein by reference. Stationary, radially mounted monitoring systems have several advantages over yoke-mounted systems, but present one notable challenge. When the monitoring system is mounted radially outwardly of the yoke, the umbilicus and/or yoke will occasionally pass through the field of vision of the monitoring system, which prevents the monitoring system from receiving an accurate picture of the interior of the centrifuge through a window of the centrifuge. This could be readily addressed were the centrifuge configured to rotate at a uniform "two omega" speed, but the centrifuge does not rotate at a uniform speed. Instead, the centrifuge rotates at a "two omega" average speed because the untwisting action of the umbilicus tends to temporarily increase the rotational speed of the centrifuge to a level that is greater than the rotational speed of the centrifuge while the umbilicus becomes twisted about its central axis. Thus, it would be advantageous to provide a system for accounting for the presence of the umbilicus and/or yoke as an obstacle to viewing the interior of the non-uniformly rotating centrifuge.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, blood processing system is provided with a centrifuge configured for rotation about a rotational axis. The centrifuge includes a radially facing window and is configured to receive at least a portion of a disposable flow circuit including an umbilicus. A yoke is configured to orbit a midsection of the umbilicus around the rotational axis at a uniform first speed so as to cause the centrifuge to rotate at a non-uniform second speed with an average speed that is approximately double the first speed. A monitoring system is positioned radially of the centrifuge, configured to directly monitor the disposable flow circuit through the window, and includes a light source, a light detector, and a controller. The light source is oriented to emit a light passing through the window when the window is rotated into alignment with the monitoring system. The light detector is oriented to receive a light reflected through the window by the centrifuge when the window is aligned with the monitoring system. The controller is configured to receive a plurality of signals from the light detector when the light detector receives reflected light during a timing cycle. A portion of the yoke and the midsection of the umbilicus are rotatable into and out of position between the monitoring system and the window when the window is aligned with the monitoring system, with that portion of the yoke being configured to receive light from the light source when it is aligned with the monitoring system and to reflect the light to the light detector. The controller is configured to determine which of the signals from the light detector during the timing cycle is caused by light reflected through the window by the centrifuge or by light reflected by the yoke. The controller compares a pulse width of each of the signals caused by light reflected through the window by the centrifuge during the timing cycle and uses the signal having the greatest pulse width to determine a characteristic of the disposable flow circuit.

In another aspect, a method is provided for determining a characteristic of a disposable flow circuit at least partially positioned within a centrifuge of the type configured for rotation about a rotational axis and including a radially facing window. The method includes rotating a yoke about the rotational axis so as to orbit a midsection of an umbilicus of the disposable flow circuit around the rotational axis at a uniform first speed, thereby causing the centrifuge to rotate at a non-uniform second speed with an average speed that is approximately double the first speed. A light is emitted from a radial position with respect to the centrifuge, with the light passing through the window and being reflected through the window by the centrifuge when the window is rotated into alignment with a light source and the yoke and umbilicus are not positioned between the light source and the window. The light is instead reflected by a portion of the yoke when the yoke is positioned between the light source and the centrifuge. The method further includes receiving reflected light a plurality of times during a timing period, converting each instance of reflected light that is received into a signal, and determining which of the signals is caused by light reflected through the window by the centrifuge or by light reflected by the yoke. A pulse width of each of the signals caused by light reflected through the window by the centrifuge during the timing cycle is compared, and the signal caused by light reflected through the window by the centrifuge having the greatest pulse width during the timing cycle is used to determine a characteristic of the disposable flow circuit.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
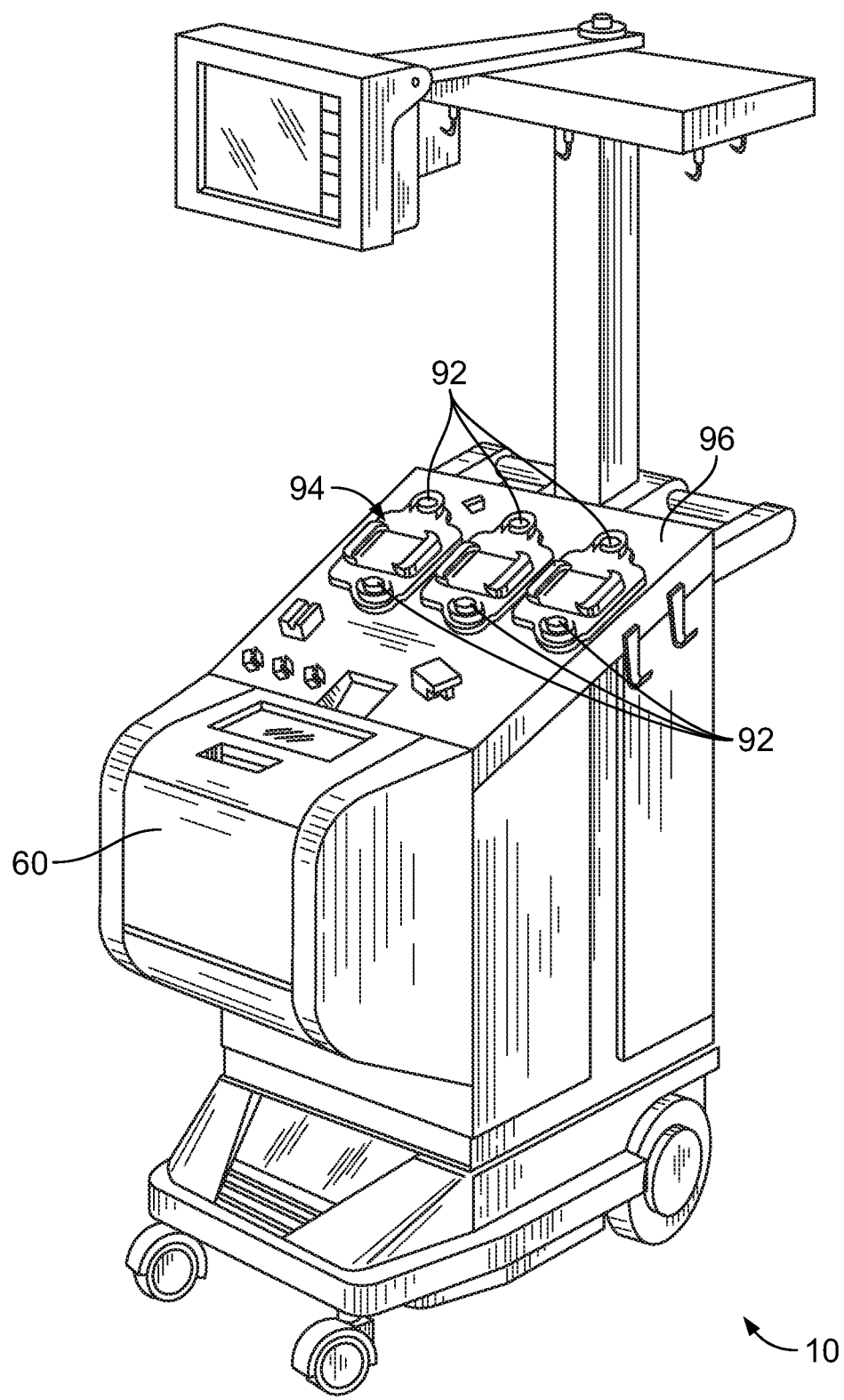
FIG. 1 is a perspective view of an exemplary blood separation device, in accordance with an aspect of the present disclosure.

Blood processing systems according to the present disclosure include a separation device, which may be variously provided without departing from the scope of the present disclosure. FIG. 1 shows an exemplary durable separation device 10 that may be employed in blood processing systems according to the present disclosure. The separation device 10 may be provided generally in accordance with the system currently marketed as the AMICUS® separator by Fenwal, Inc. of Lake Zurich, Ill., which is an affiliate of Fresenius Kabi AG of Bad Homburg, Germany, as described in greater detail in U.S. Pat. No. 5,868,696, which is hereby incorporated herein by reference. The separation device 10 can be used for processing various fluids, but is particularly well suited for processing whole blood and other suspensions of biological cellular materials. While fluid treatment principles will be described herein with reference to one particular system, it should be understood that these principles may be employed with other blood processing systems and separation devices without departing from the scope of the present disclosure.

Figure 2:
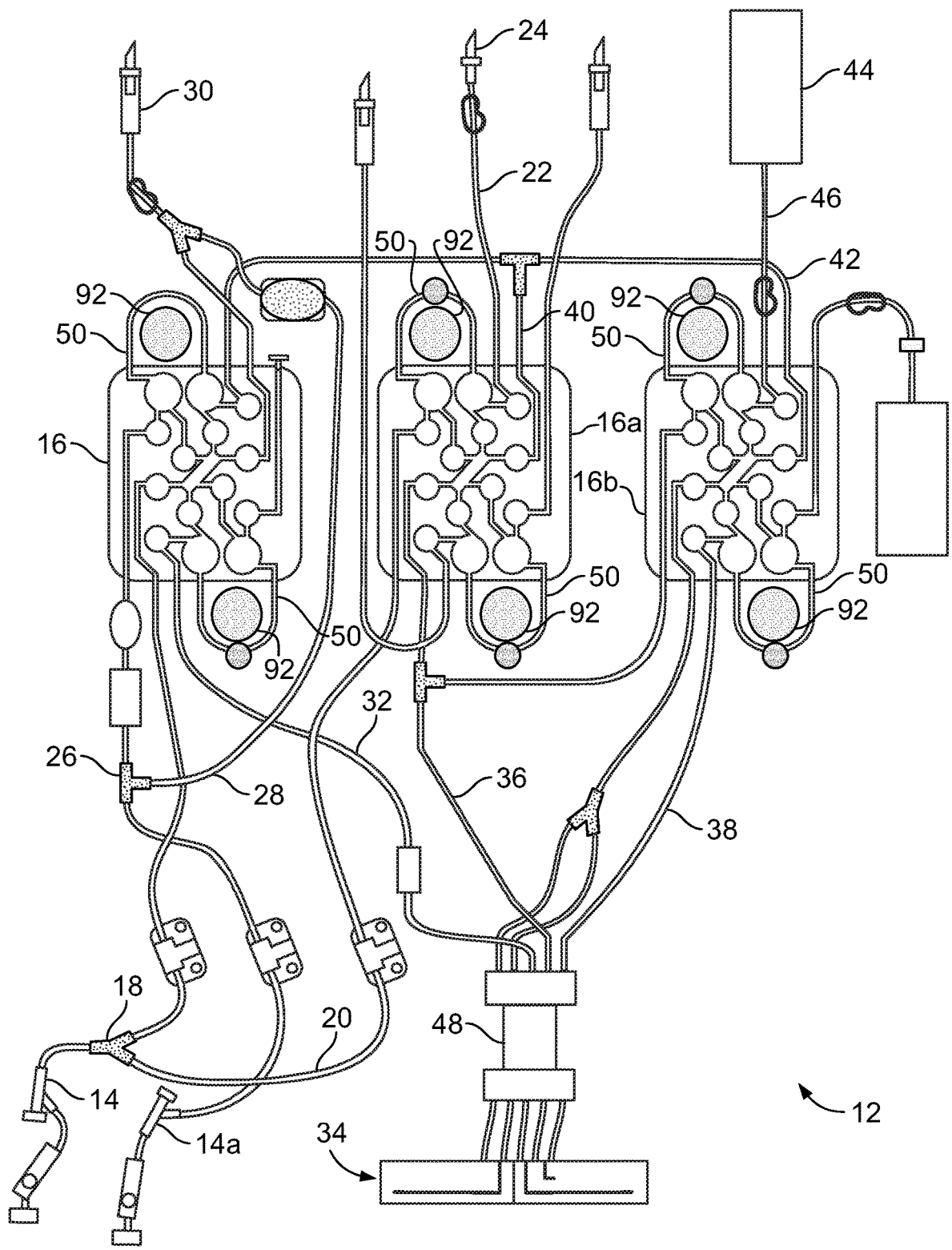
FIG. 2 is a diagrammatic view of an exemplary disposable flow circuit that may be used in combination with the separation device of FIG. 1.

FIG. 2 illustrates a disposable flow circuit 12 that may be used in combination with the separation device 10 of FIG. 1 to provide a blood processing system. The flow circuit 12 includes a variety of tubing and a number of components, only some of which will be described herein in greater detail. It should be understood that FIG. 2 illustrates only one example of a flow circuit which may be used in combination with the separation device 10 of FIG. 1 and differently configured flow circuits may also be employed without departing from the scope of the present disclosure.

The illustrated flow circuit 12 is a "two needle" system, which includes a pair of blood source access devices 14 and 14a (e.g., phlebotomy needles) for fluidly connecting a blood source with the flow circuit 12. The blood source access devices 14 and 14a are connected by tubing to a left cassette 16, which will be described in greater detail herein. One of the blood source access devices 14 is used to draw blood from the blood source into the flow circuit 12 and is connected to the left cassette 16 by a y-connector 18. The other leg of the y-connector 18 is connected to tubing 20 which leads to a middle cassette 16a. The tubing 20 is connected, through the middle cassette 16a, to additional tubing 22, which includes a container access device 24 (e.g., a sharpened cannula or spike connector) for accessing the interior of an anticoagulant container (not illustrated). During a blood treatment operation, anticoagulant from the anticoagulant container may be added to the blood from the blood source at the y-connector 18 prior to entering the left cassette 16.

The other blood source access device 14a is used to deliver or return blood, a blood component, and/or some other replacement fluid to the blood source and is also connected to the left cassette 16 by a y-connector 26. The other leg of the y-connector 26 is connected to tubing 28 connected at its other end to a container access device 30. Although not illustrated, the container access device 30 may be associated with a container having an amount of fluid (e.g., saline) to be used to prime the flow circuit 12 and/or delivered to the blood source via the blood source access device 14a.

The left cassette 16 also includes tubing 32 which is connected to a blood separation chamber 34 of the flow circuit 12 for flowing anticoagulated blood thereto. The blood separation chamber 34 separates the blood into its constituent parts (as will be described in greater detail herein) and returns the blood components to the flow circuit 12. In one embodiment, one separated blood component (e.g., cellular blood components) is returned to the middle cassette 16a of the flow circuit 12 from the blood separation chamber 34 via tubing 36, while another separated blood component (e.g., substantially cell-free plasma) is returned to a right cassette 16b of the flow circuit 12 from the blood separation chamber 34 via tubing 38. The first separated component may be pumped to the left cassette 16 via tubing 40, where it is returned to the blood source. The second separated component may be pumped back to the left cassette 16 via tubing 42 for return to the blood source and/or it may be pumped into a container 44 via different tubing 46. The destination of the second separated component (and the other fluids passing through the cassettes) depends upon the actuation of the various valves of the cassettes, as will be described in greater detail herein. The various tubes connected to the blood separation chamber 34 are bundled in an umbilicus 48, which will be described in greater detail herein.

Additional tubing may be connected from one port of a cassette to another port of the same cassette, so as to form tubing loops 50 which interact with a fluid flow element or pump to flow fluid through the flow circuit 12, as will be described in greater detail herein.

A. The Centrifuge

Figure 3:
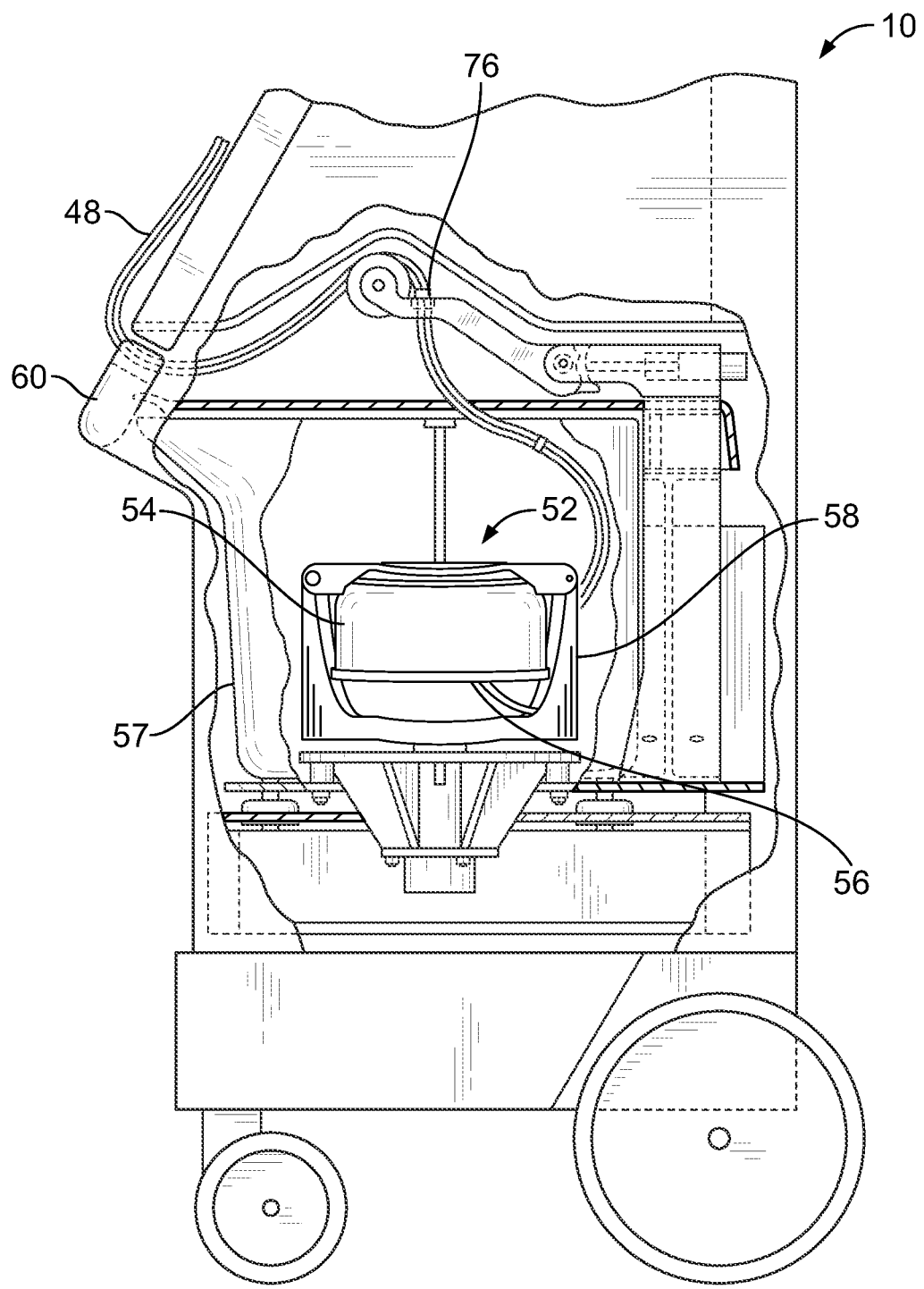
FIG. 3 is a side elevational view, with portions broken away and in section, of the separation device of FIG. 1, with a centrifuge bowl and spool of the system being shown in their operating position.
Figure 4:
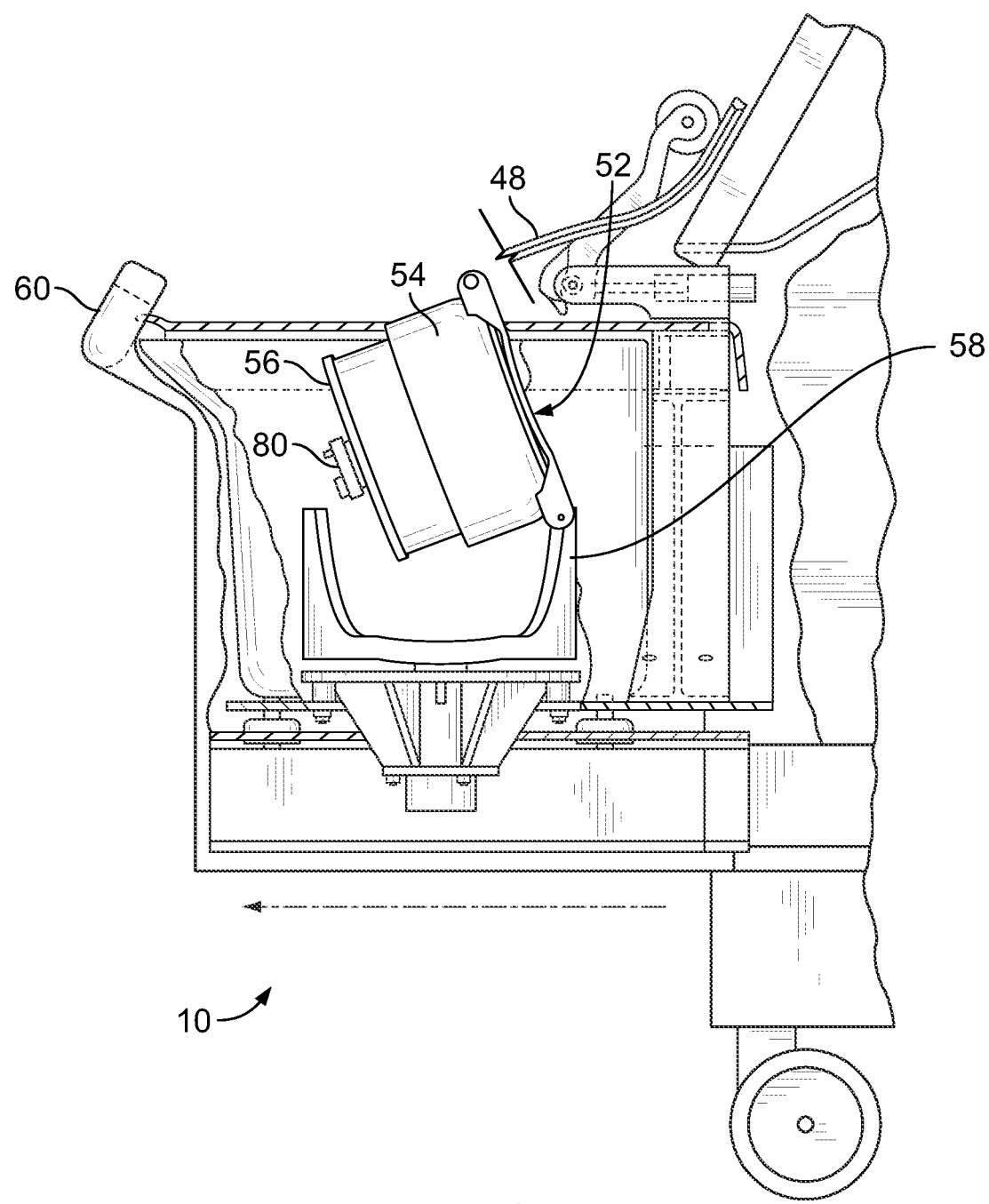
FIG. 4 is a side elevational view, with portions broken away and in section, of the separation device of FIG. 1, with the centrifuge bowl and spool shown in an upright position for receiving a blood separation chamber.
Figure 16:
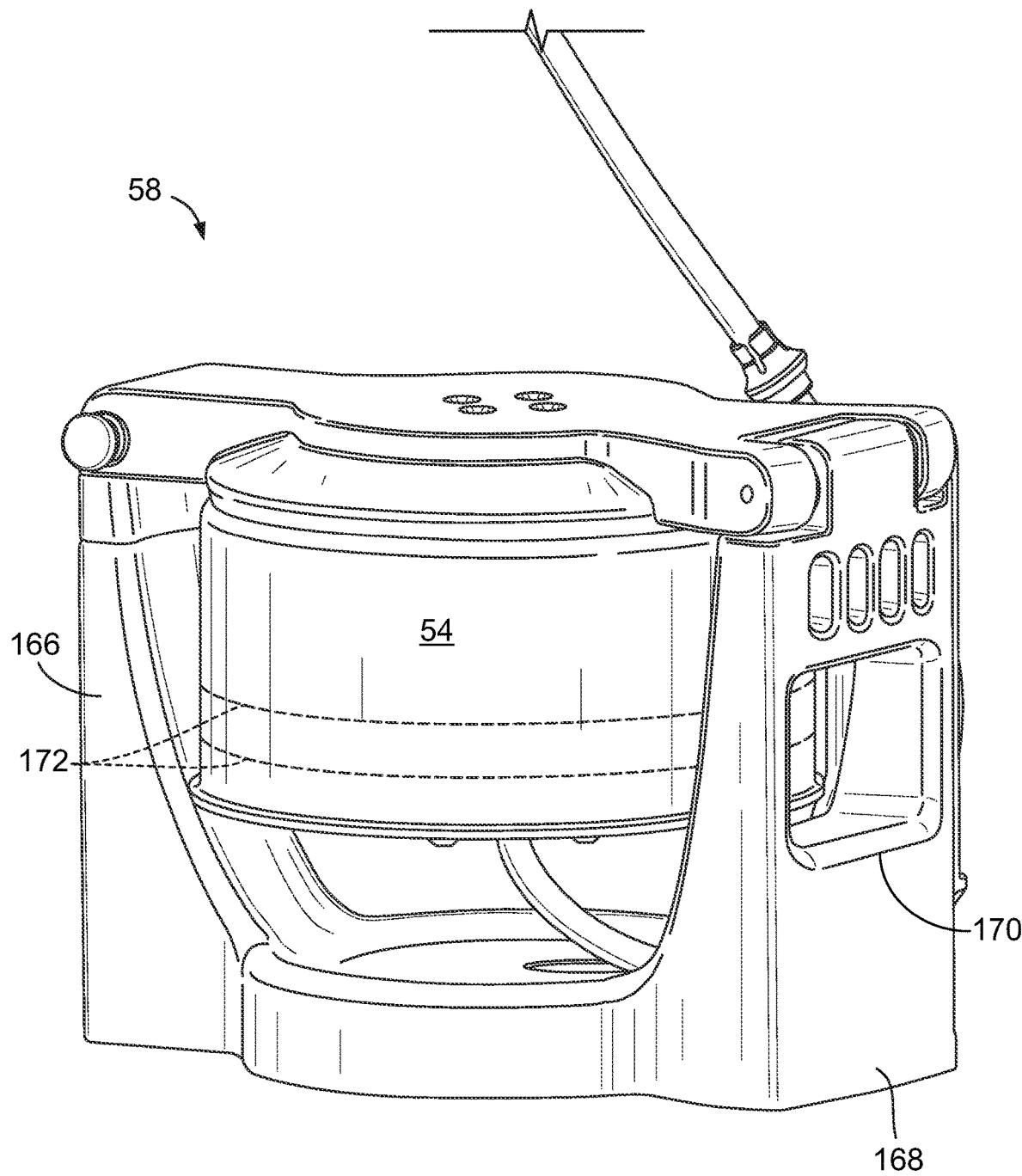
FIG. 16 is a perspective view of the yoke of the centrifuge of FIGS. 3 and 4.

The separation device 10 includes a centrifuge 52 (FIGS. 3 and 4) used to centrifugally separate blood components. The separation device 10 may be programmed to separate blood into a variety of components (e.g., platelet-rich plasma and red cells). The illustrated centrifuge 52 is of the type shown in U.S. Pat. No. 5,316,667. The centrifuge 52 comprises a bowl 54 and a spool 56 which are received within a bucket 57. The bowl 54 and spool 56 are pivoted on a yoke 58 (shown in greater detail in FIGS. 16 and 17) between an operating position (FIG. 3) and a loading/unloading position (FIG. 4). The centrifuge 52 is housed within the bucket 57 in the interior of the separation device 10, so a door 60 is provided to allow access to the centrifuge 52 for loading and unloading the blood separation chamber 34, as will be described in greater detail herein. The door 60 remains closed during operation to protect and enclose the centrifuge 52.

When in the loading/unloading position, the spool 56 can be opened by movement at least partially out of the bowl 54, as FIG. 4 shows. In this position, the operator wraps the flexible blood separation chamber 34 about the spool 56 (see FIG. 5). Closure of the spool 56 and bowl 54 encloses the chamber 34 for processing. When closed, the spool 56 and bowl 54 are pivoted into the operating position of FIG. 3 for rotation about an axis.

B. The Blood Separation Chamber

Figure 6:
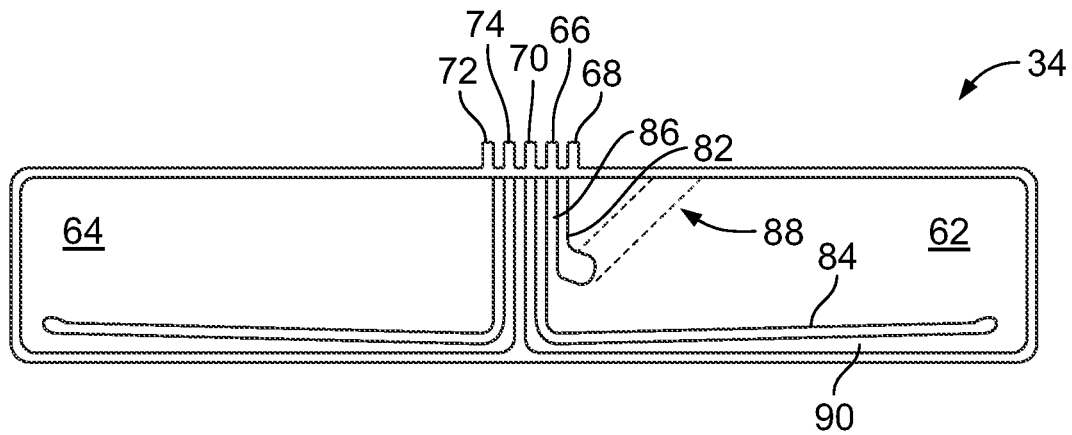
FIG. 6 is a plan view of the blood separation chamber of FIG. 5, out of association with the spool.

FIG. 6 shows a representative embodiment of a blood separation chamber 34 which may be used in connection with the present disclosure. The chamber 34 shown in FIG. 6 allows for either single- or multi-stage processing. The illustrated chamber 34 has first and second stages 62 and 64, with only one of the stages (typically, the first stage 62) being used for fluid separation in a single-stage procedure and both stages 62 and 64 being used for fluid separation in a multi-stage procedure.

Figure 5:
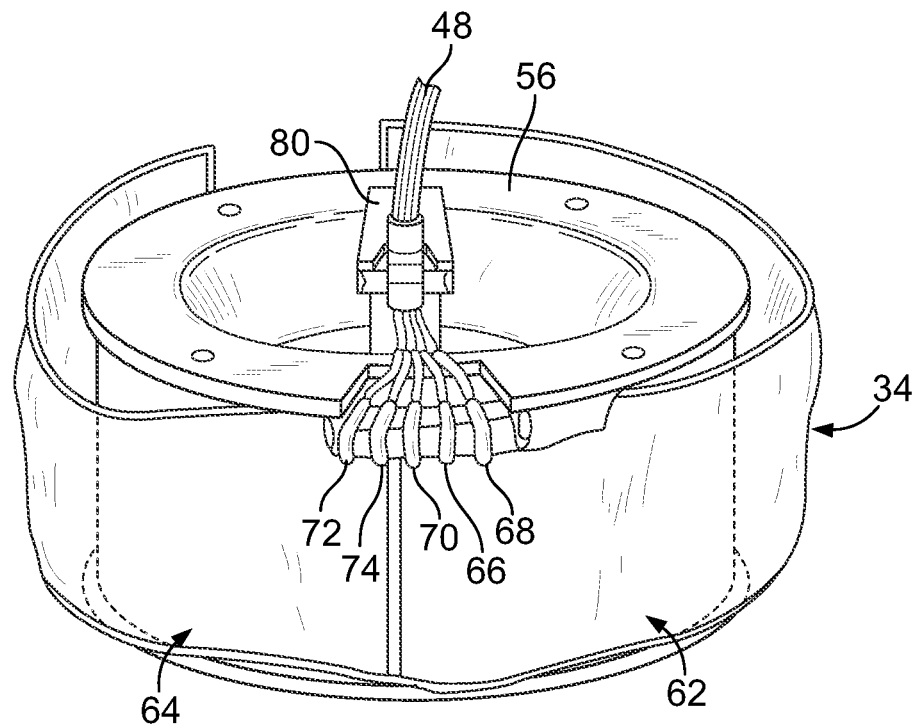
FIG. 5 is a top perspective view of the centrifuge spool of FIG. 4 in its upright position and carrying the blood separation chamber of the flow circuit of FIG. 2.

As FIGS. 5 and 6 best illustrate, there are three ports 66, 68, and 70 associated with the first stage 62, with one serving as an inlet port and the other two serving as outlet ports. For example, in one embodiment, the port identified at 70 is used for conveying blood from a blood source into the first stage 62, while the other two ports 66 and 68 serve as outlet ports for passing separated blood components from the first stage 62 to the flow circuit 12 (via tubing 36 and 38, respectively). More particularly, the first outlet port 68 conveys a low density blood component from the first stage 62, while the second outlet port 66 conveys a high density blood component from the first stage 62.

In a method of carrying out single-stage processing, one of the separated components is returned to the blood source, while the other is removed from the first stage 62 for collection and/or further processing. If multi-stage processing is required, one of the components will be transferred from the first stage 62 to the second stage 64 via a port 72 associated with the second stage 64. The component transferred to the second stage 64 is further fractionated into sub-components, with one of the sub-components being removed from the second stage 64 via an outlet port 74 and the other sub-component remaining in the second stage 64.

As best shown in FIG. 5, the tubing umbilicus 48 of the flow circuit 12 is attached to the ports 66, 68, 70, 72, and 74. The umbilicus 48 interconnects the first and second stages 62 and 64 with each other and with the components of the flow circuit 12 positioned outside of the centrifuge 52. As FIG. 3 shows, a non-rotating ("zero omega") holder 76 holds the upper portion of the umbilicus 48 in a non-rotating position above the spool 56 and bowl 54. A holder 78 on the yoke 58 (FIG. 17) rotates the mid-portion of the umbilicus 48 at a first ("one omega") speed about the suspended spool 56 and bowl 54. Another holder 80 (FIGS. 4 and 5) fixedly secures the lower end of the umbilicus 48 to the spool 56 and bowl 54 in a way that causes the spool 56 and bowl 54 to rotate at an average speed that is twice the one omega speed ("two omega"), due to the midsection of the umbilicus 48 being rotated at the one omega speed combined with the tendency of the umbilicus 48 to untwist in opposition to becoming twisted.

As FIG. 6 shows, a first interior seal 82 is located between the low density outlet port 68 and the high density outlet port 66. A second interior seal 84 is located between the high density outlet port 66 and the blood inlet port 70. The interior seals 82 and 84 form a fluid passage 86 (an outlet for high density blood components in an exemplary procedure) and a low density collection region 88 in the first stage 62. The second seal 84 also forms a fluid passage 90 (a blood inlet in an exemplary procedure) in the first stage 62. The second stage 64 may also include an interior seal to define a flow path between its ports 72 and 74.

C. The Cassettes

Blood entering the blood separation chamber 34 is pumped thereinto by one or more pumps 92 of the separation device 10 (FIGS. 1 and 2) acting upon one or more of the tubing loops 50 extending from the cassettes 16-16b of the flow circuit 12 (FIG. 2). An exemplary cassette 16 is illustrated in greater detail in FIGS. 7 and 8, while the pumps 92 and associated cassette holder 94 are shown in greater detail in FIG. 9.

Before beginning a given blood processing and collection procedure, the operator loads various components of the flow circuit 12 onto the sloped front panel 96 and into the centrifuge 52 of the separation device 10. As described above, the blood separation chamber 34 and the umbilicus 48 of the flow circuit 12 are loaded into the centrifuge 52, with a portion of the umbilicus 48 extending outside of the interior of the separation device 10, as shown in FIG. 3. The sloped front panel 96 of the separation device 10 includes at least one cassette holder 94 (three in the illustrated embodiment), each of which is configured to receive and grip an associated cassette 16-16b of the flow circuit 12.

Figure 7:
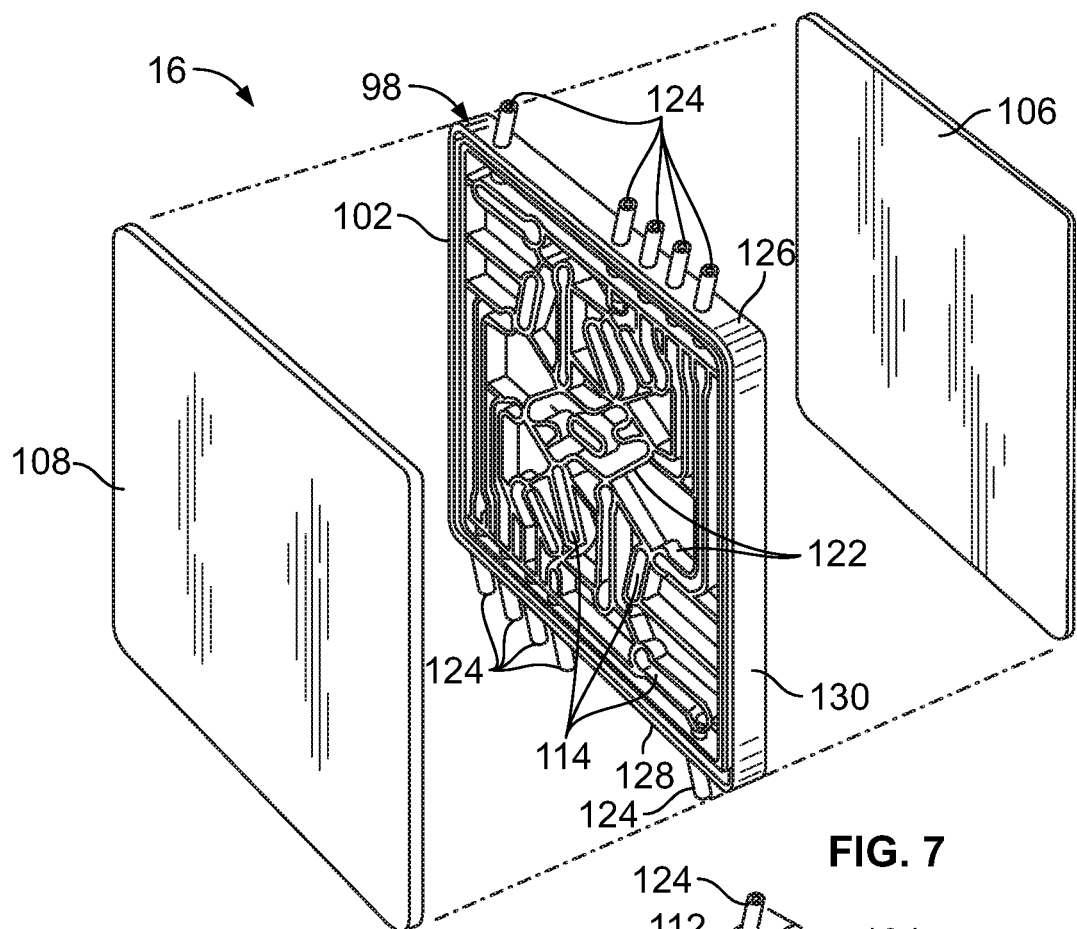
FIG. 7 is an exploded perspective view of a fluid processing cassette of the flow circuit of FIG. 2.
Figure 8:
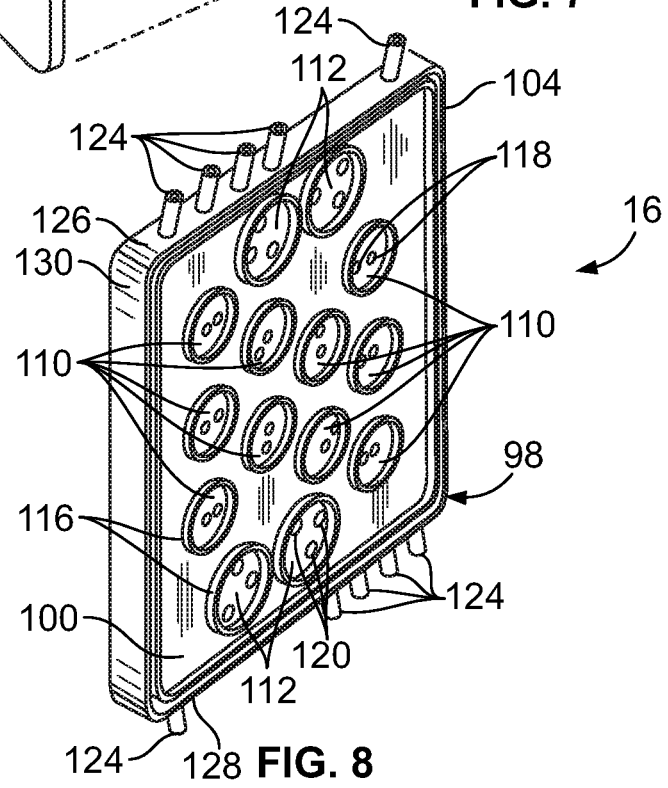
FIG. 8 is a perspective view of an underside of the fluid processing cassette of FIG. 7.
Figure 9:
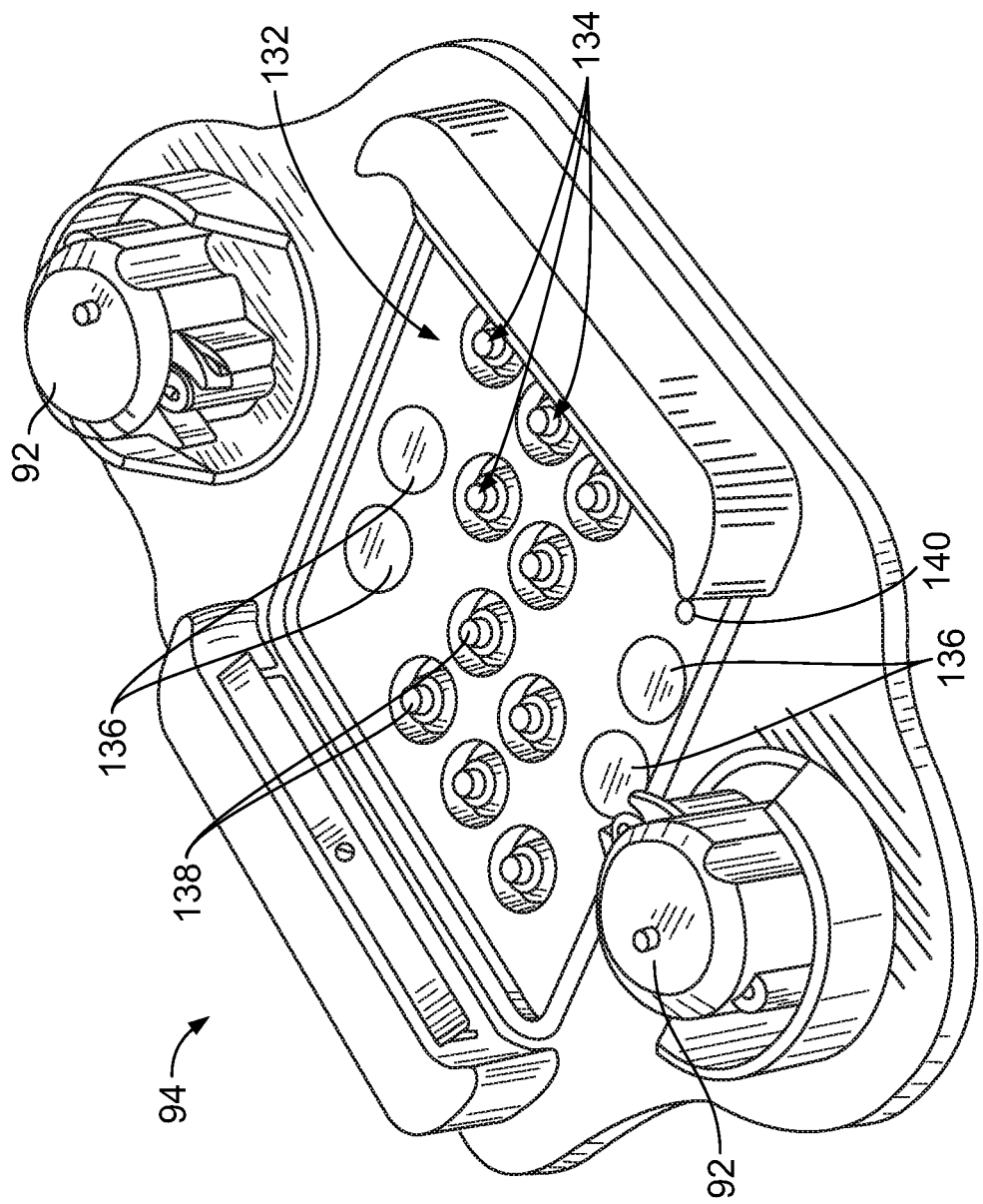
FIG. 9 is a perspective view of a cassette holder of the blood processing system of FIG. 1.

Each cassette 16-16b, one of which is shown in FIGS. 7 and 8, includes an injection molded body 98 that is compartmentalized by an interior wall 100 (FIG. 8) to present or form a topside 102 (FIG. 7) and an underside 104 (FIG. 8). For the purposes of description, the topside 102 is the side of the cassette 16 that, in use, faces away from the separation device 10, while the underside 104 faces towards the separation device 10. A flexible diaphragm 106 overlies and peripherally seals the underside 104 of the cassette 16. A generally rigid upper panel 108 overlies the topside 102 of the cassette 16 and is sealed peripherally and to the raised channel-defining walls in the cassette 16, as described later.

In one embodiment, the cassette 16, the interior wall 100, and the upper panel 108 are made of a rigid medical grade plastic material, while the diaphragm 106 is made of a flexible sheet of medical grade plastic. The upper panel 108 and the diaphragm 106 are sealed about their peripheries to the peripheral edges of the top- and undersides 102, 104 of the cassette 16, respectively.

As shown in FIGS. 7 and 8, the top- and undersides 102 and 104 of the cassette 16 include preformed cavities. On the underside 104 of the cassette 16 (FIG. 8), the cavities form an array of valve stations 110 and an array of pressure sensing stations 112. On the topside 102 of the cassette 16 (FIG. 7), the cavities form an array of channels or paths 114 for conveying liquids. The valve stations 110 communicate with the liquid paths 114 through the interior wall 100 to interconnect them in a predetermined manner. The sensing stations 112 also communicate with the liquid paths 114 through the interior wall 100 to sense pressures in selected regions. The number and arrangement of the liquid paths 114, the valve stations 110, and the sensing stations 112 can vary but, in the illustrated embodiment, the cassette 16 provides nineteen liquid paths 114, ten valve stations 110, and four sensing stations 112.

The valve and sensing stations 110, 112 resemble shallow wells open on the cassette underside 104 (FIG. 8). Upstanding edges 116 rise from the interior wall 100 and peripherally surround the valve and sensing stations 110, 112. The valve stations 110 are closed by the interior wall 100 on the topside 102 of the cassette 16, except that each valve station 110 includes a pair of through holes or ports 118 in the interior wall 100. The ports 118 each open into selected different liquid paths 114 on the topside 102 of the cassette 16.

The sensing stations 112 are likewise closed by the interior wall 100 on the topside 102 of the cassette 16, except that each sensing station 112 includes three through holes or ports 120 in the interior wall 100 (FIG. 8). The ports 120 open into selected liquid paths 114 on the topside 102 of the cassette 16. These ports 120 channel liquid flow among the selected liquid paths 114 through the associated sensing station 112.

In one embodiment, the flexible diaphragm 106 overlying the underside 104 of the cassette 16 is sealed by ultrasonic welding to the upstanding peripheral edges 116 of the valve and sensing stations 110, 112. This isolates the valve stations 110 and sensing stations 112 from each other and the rest of the system. In an alternative embodiment, the flexible diaphragm 106 can be seated against the upstanding edges 116 by an external positive force applied by the cassette holder 94 against the diaphragm 106. The positive force, like the ultrasonic weld, peripherally seals the valve and sensing stations 110, 112.

The localized application of additional positive force (referred to herein as a "closing force") upon the intermediate region of the diaphragm 106 overlying a valve station 110 serves to flex the diaphragm 106 into the valve station 110. Such closing force is provided by the cassette holder 94, as will be described in greater detail herein. The diaphragm 106 seats against one of the ports 118 to seal the port 118, which closes the valve station 110 to liquid flow. Upon removal of the closing force, fluid pressure within the valve station 110, the application of a vacuum to the outer surface of the diaphragm 106, and/or the plastic memory of the diaphragm 106 itself unseats the diaphragm 106 from the port 118, opening the valve station 110 to liquid flow.

Upstanding channel sides or edges 122 rise from the interior wall 100 to peripherally surround and define the liquid paths 114, which are open on the topside 102 of the cassette 16. The liquid paths 114 are closed by the interior wall 100 on the underside 104 of the cassette 16, except for the ports 118, 120 of the valve and sensing stations 110, 112 (FIG. 8). The rigid panel 108 overlying the topside 102 of the cassette 16 is sealed by ultrasonic welding to the upstanding peripheral edges 122, sealing the liquid paths 114 from each other and the rest of the system.

In the illustrated embodiment, ten pre-molded tube connectors 124 extend out along opposite side edges 126, 128 of each cassette 16. The tube connectors 124 are arranged five on one side edge 126 and five on the other side edge 128. The other side edges 130 of the cassette 16, as illustrated, are free of tube connectors. The tube connectors 124 are associated with external tubing (FIG. 2) to associate the cassettes 16 with the remainder of the flow circuit 12, as described above.

The tube connectors 124 communicate with various interior liquid paths 114, which constitute the liquid paths of the cassette 16 through which a fluid enters or exits the cassette 16. The remaining interior liquid paths 114 of the cassette 16 constitute branch paths that link the liquid paths 114 associated with the tube connectors 124 to each other through the valve stations 110 and sensing stations 112.

D. The Cassette Holders and Pumps

Turning now to the cassette holders 94 (FIG. 9), each receives and grips one of the cassettes 16-16b along the two opposed sides edges 130 in the desired operating position. The cassette holder 94 includes a pair of peristaltic pump stations 92. When the cassette 16 is gripped by the cassette holder 94, tubing loops 50 extending from the cassette 16 (FIG. 2) make operative engagement with the pump stations 92. The pump stations 92 are operated to cause fluid flow through the cassette 16.

The flexible diaphragm 106 covering the underside 104 of the cassette 16 is urged into intimate contact with a valve and sensor array or assembly 132 by the cassette holder 94. The valve assembly 132 acts in concert with the valve stations 110 and sensing stations 112 of the cassette 16. The valve assembly 132 illustrated in FIG. 9 includes ten valve actuators 134 and four pressure sensing transducers 136. The valve actuators 134 and the pressure sensing transducers 136 are mutually arranged in the same layout as the valve stations 110 and sensing stations 112 on the underside 104 of the cassette 16. When the cassette 16 is gripped by the cassette holder 94, the valve actuators 134 align with the cassette valve stations 110. At the same time, the pressure sensing transducers 136 mutually align with the cassette sensing stations 112.

In one embodiment, each valve actuator 134 includes an electrically actuated solenoid pin or piston 138. Each piston 138 is independently movable between an extended position and a retracted position. When in its extended position, the piston 138 presses against the region of the diaphragm 106 that overlies the associated valve station 110. In this position, the piston 138 flexes the diaphragm 106 into the associated valve station 110, thereby sealing the associated valve port 118. This closes the valve station 110 to liquid flow. When in its retracted position, the piston 138 does not apply force against the diaphragm 106. As before described, the plastic memory of the diaphragm 106 may be such that the removal of force is sufficient for the diaphragm to unseats from the valve port 118, thereby opening the valve station 110 to liquid flow. Alternatively, a vacuum may be applied to the diaphragm 106, for example by the vacuum port 140 illustrated in FIG. 9, to actively unseat the diaphragm 106 from the valve port 118.

The pressure sensing transducers 136 sense liquid pressures in the sensing stations 112 of the cassette 16. The sensed pressures are transmitted to a controller of the separation device 10 as part of its overall system monitoring function. If provided, the vacuum port 140 of the cassette holder 94 may provide suction to the diaphragm 106 of the cassette 16, drawing it into close contact with the transducers 136 for more accurate pressure readings.

E. Blood Separation

As described above, the centrifuge 52 rotates the blood separation chamber 34, thereby centrifugally separating whole blood received from a blood source into component parts, e.g., red blood cells, plasma, and buffy coat or interface comprising platelets and leukocytes.

Figure 10:
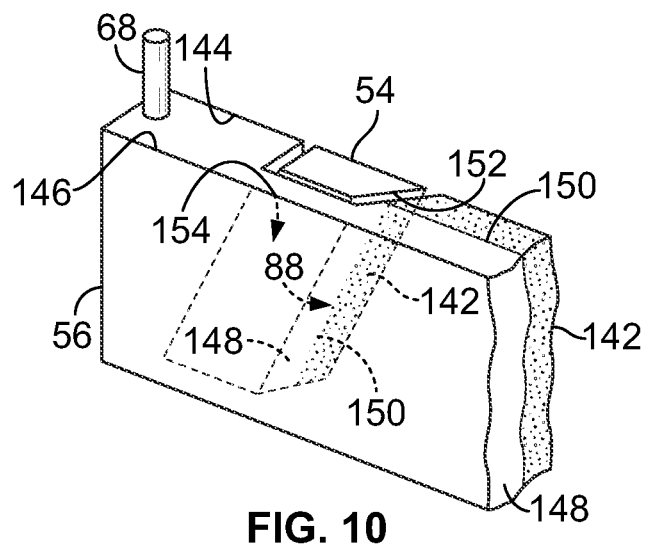
FIG. 10 is an enlarged perspective view of an interface ramp carried by the centrifuge in association with the blood separation chamber, showing the centrifugally separated red blood cell layer, plasma layer, and interface within the chamber when in a desired location on the ramp.

In an exemplary procedure, the fluid passage 90 channels blood directly into the circumferential flow path immediately next to the low density collection region 88. As shown in FIG. 10, the blood separates into an optically dense layer 142 containing cellular components, which forms as cellular components move under the influence of centrifugal force toward the high-G (outer) wall 144 or bowl 54. The optically dense layer 142 will include red blood cells (and, hence, will be referred to herein as the "RBC layer") but, depending on the speed at which the centrifuge 52 is spun, other cellular components (e.g., larger white blood cells and platelets) may also be present in the RBC layer 142.

The movement of the component(s) of the RBC layer 142 displaces less dense blood components radially toward the low-G (inner) wall 146 or spool 56, forming a second, less optically dense layer 148. The less optically dense layer 148 includes plasma (and, hence, will be referred to herein as the "plasma layer") but, depending on the speed at which the centrifuge 52 is rotated and the length of time that the blood is resident in the centrifuge, other components (e.g., platelets and smaller white blood cells) may also be present in the plasma layer 148.

The transition between the formed cellular blood components and the liquid plasma component is generally referred to as the interface 150 (FIG. 10). Platelets and white blood cells (which have a density greater than plasma and usually less than red blood cells) typically occupy this transition region, although that also varies with centrifuge speed and residence time, as is well known in the technical field.

Figure 11:
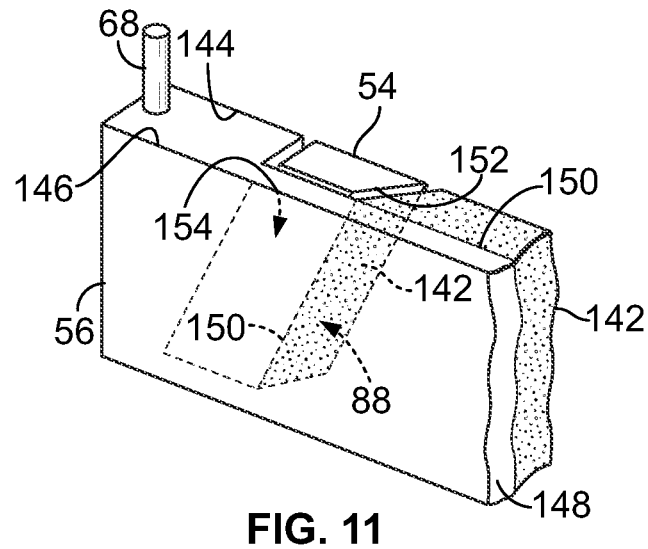
FIG. 11 is an enlarged perspective view of the interface ramp shown in FIG. 10, showing the red blood cell layer and interface at an undesired high location on the ramp.
Figure 12:
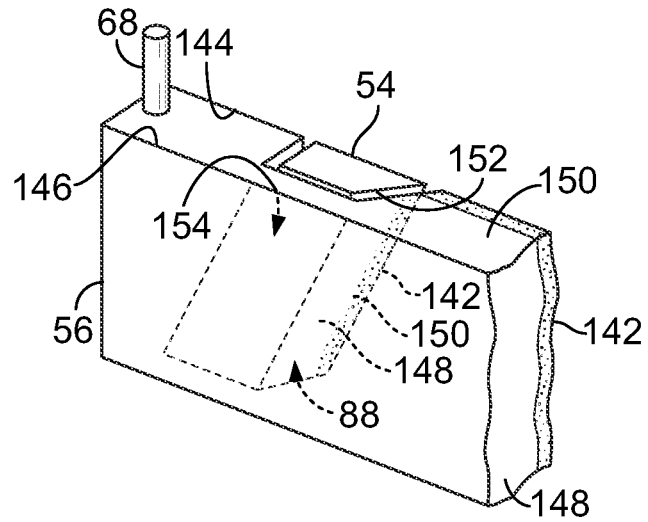
FIG. 12 is an enlarged perspective view of the interface ramp shown in FIG. 10, showing the red blood cell layer and interface at an undesired low location on the ramp.

The location of the interface 150 within the chamber 34 can dynamically shift during blood processing, as shown in FIGS. 11 and 12. If the location of the interface 150 is too high (that is, if it is too close to the low-G wall 146 and the removal port 68, as FIG. 11 shows), cellular components can spill over and into the low density collection region 88, adversely affecting the quality of the low density components (typically plasma). On the other hand, if the location of the interface 150 is too low (that is, if it resides too far away from the low-G wall 146, as FIG. 12 shows), the collection efficiency of the separation device 10 may be impaired.

As FIG. 10 shows, a ramp 152 extends from the high-G wall 144 of the bowl 54 at an angle across the low density collection region 88. The angle, measured with respect to the axis of the first outlet port 68 is about 30° in one embodiment. FIG. 10 shows the orientation of the ramp 88 when viewed from the low-G wall 146 of the spool 56. FIG. 6 shows, in phantom lines, the orientation of the ramp 152 when viewed from the high-G wall 144 of the bowl 54. As FIG. 10 shows (and as will be described in greater detail), the ramp 152 makes the interface 150 between the RBC layer 142 and the plasma layer 148 more discernible for detection, displaying the RBC layer 142, plasma layer 148, and interface 150 for viewing through the high-G wall 144 of the chamber 34. Further details of the angled relationship of the ramp 152 and the first outlet port 68 can be found in U.S. Pat. No. 5,632,893, which is incorporated herein by reference.

The ramp 152 forms a tapered wedge that restricts the flow of fluid toward the first outlet port 68. The top edge of the ramp 152 extends to form a constricted passage 154 along the low-G wall 146. The plasma layer 148 must flow through the constricted passage 154 to reach the first outlet port 68. As the plasma layer 148 exits the first stage 62 via the first outlet port 68, the RBC layer 142 (which is prevented from reaching the plasma outlet port 68) exits the first stage 64 through the high density outlet port 66. The separated components may be collected for further processing or as a waste product or may be returned to the blood source.

In a multi-stage procedure, the plasma layer 148 (typically comprising platelet-rich plasma if the fluid separated in the first stage 62 is whole blood) is conveyed out of the first stage 62 and into the second stage 64 via one of the second stage ports 72 (passing through one of the cassettes between the first and second stages 62 and 64). As the plasma layer 148 is being conveyed into the second stage 64, the RBC layer 142 exiting the first stage 64 through the high density outlet port 66 may be collected for further processing or as a waste product or may be returned to the blood source (as in the exemplary single-stage procedure).

The same rotation of the chamber 34 within the centrifuge 52 that separates the RBC layer 142 from the plasma layer 148 also causes the plasma layer 148 in the second stage 64 to be further fractionated into two subcomponents. For example, if the plasma layer 148 flowing into the second stage 64 is platelet-rich plasma, then concentrated or pelleted platelets are separated from platelet-poor plasma in the second stage 64. In this case, the platelet-poor plasma may flow out of the second stage 64 via the other second stage port 74 while platelets continue to accumulate in the second stage 64. The platelet-poor plasma conveyed out of the second stage 64 may be collected for further processing or as a waste product or may be returned to the blood source.

The concentrated platelets may remain in the second stage 64 (e.g., as a waste product) or, alternatively, the platelets may instead be resuspended once a target amount of platelets have been accumulated in the second stage 64 or once a predetermined amount of blood has been processed. In this case, the platelets may be resuspended using the platelet-poor plasma previously separated from the platelets, a synthetic platelet additive solution, or a different fluid or combination of fluids.

The resuspended platelets may then be conveyed out of the second stage 64 and into a collection container for storage, which may include further processing, such as light inactivation.

Further details of the separation chamber 34 and its operation may be found in U.S. Pat. No. 5,316,667.

F. The Optical Monitoring System

Figure 13:
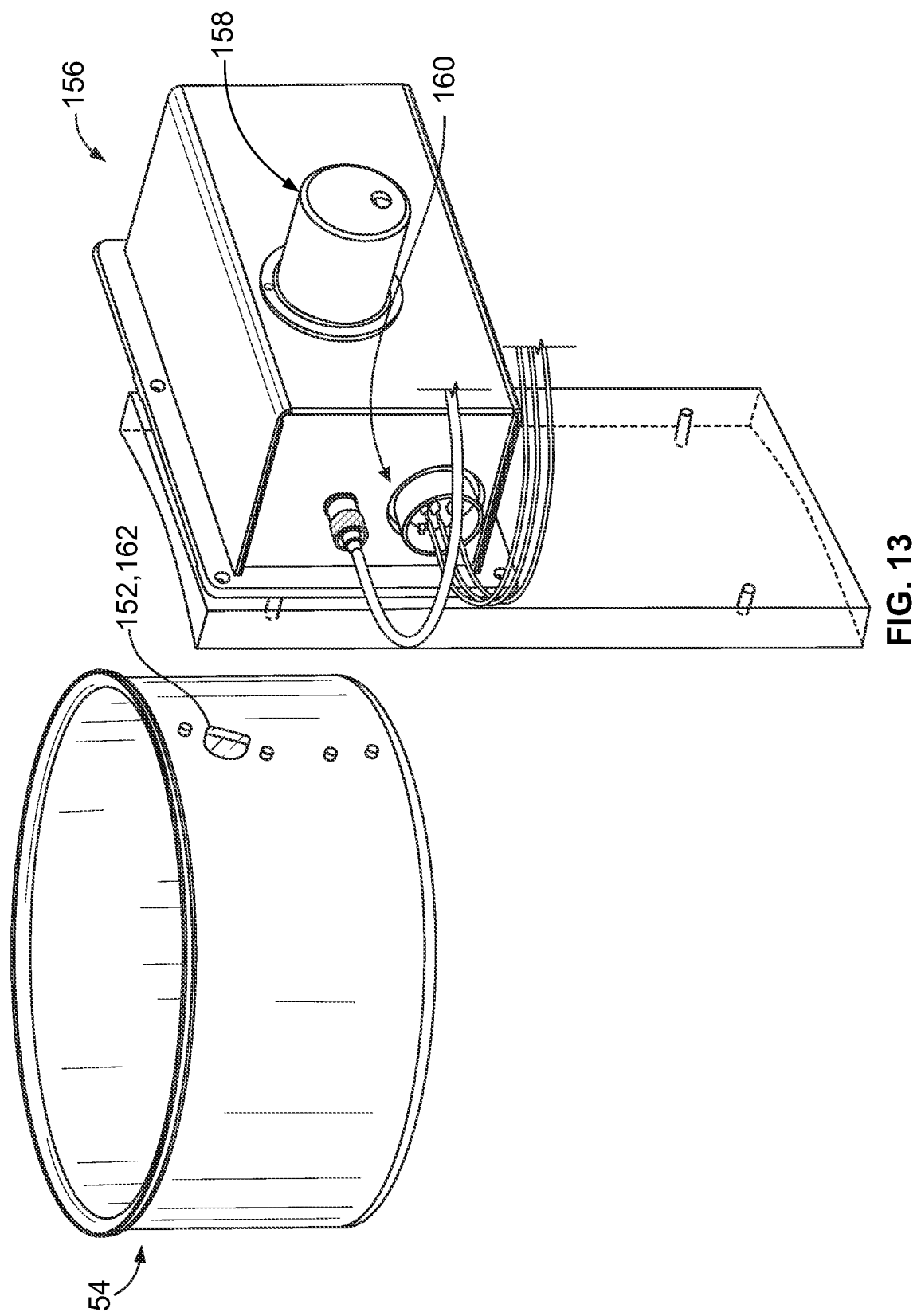
FIG. 13 is a front perspective view of the bowl of the centrifuge of FIGS. 3 and 4 and an optical monitoring system mounted to a stationary surface of the centrifuge.
Figure 14:
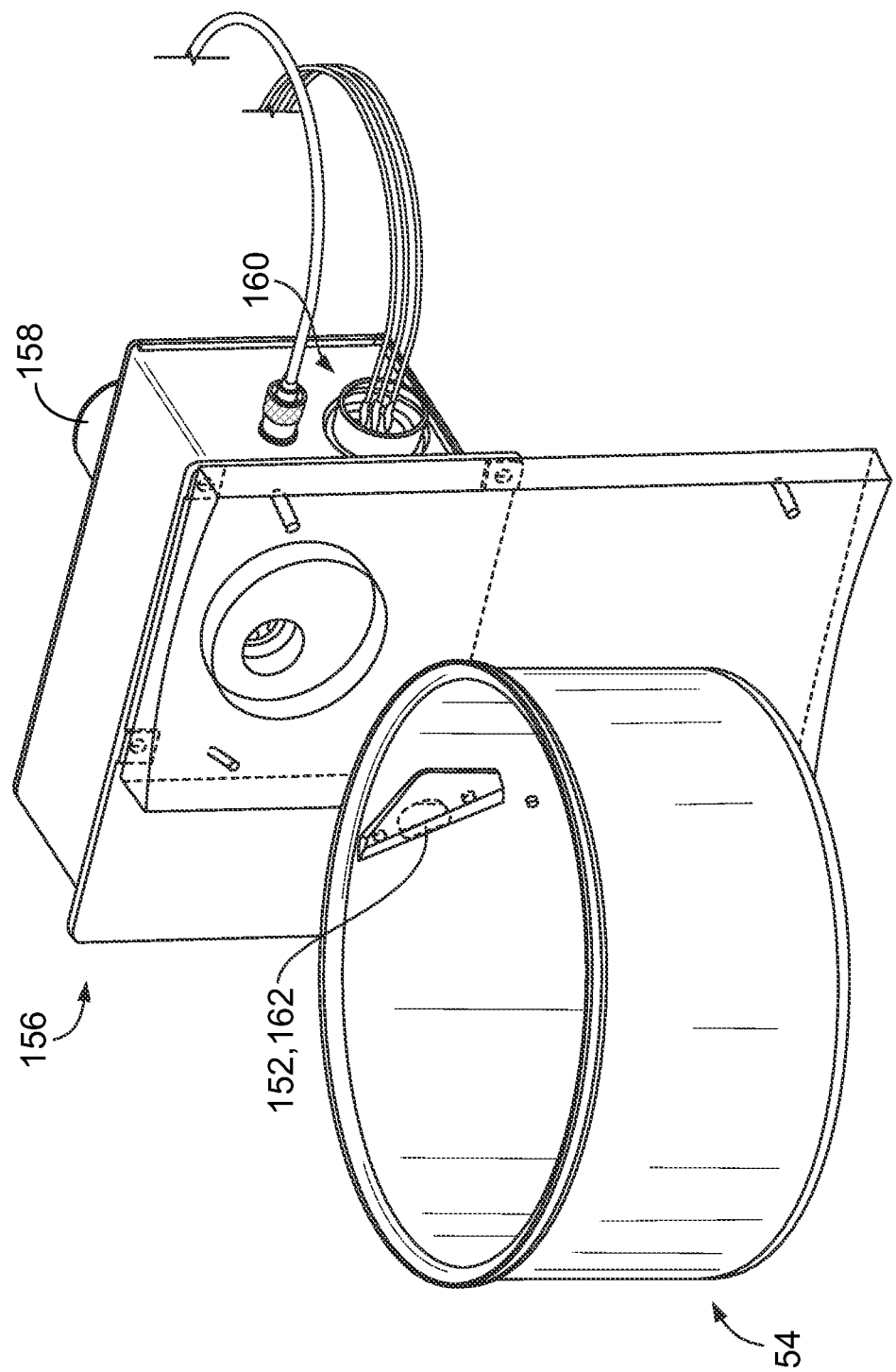
FIG. 14 is a rear perspective view of the bowl and optical monitoring system of FIG. 13.

The separation device 10 includes an optical monitoring system 156 (FIGS. 13 and 14), which is configured to directly monitor the disposable flow circuit 12 in the centrifuge 52. The illustrated monitoring system 156 includes a light source 158 and a light detector or image sensor 160. In addition to detecting characteristics of flow through the flow circuit 12 (e.g., the location of the interface 150 on the ramp 152), the monitoring system 156 may be configured to detect other information about the flow circuit 12 itself (such as, but not limited to, placement, positioning, and suitability of the circuit).

The light source 158 of the monitoring system 156 is positioned and oriented to illuminate a portion of the flow circuit 12 received within the centrifuge 52 (i.e., the blood separation chamber 34). The monitoring system 156 is not limited to one light source 158, but may include a plurality of light sources. If the monitoring system 156 includes a plurality of light sources, the lights produced may have different wavelengths. The light sources may be operated simultaneously or independently of each other (e.g., sequentially). The light source 158 may be variously configured without departing from the scope of the present disclosure. For example, the light source 158 may include at least one light emitting diode or laser diode, but may alternatively (or additionally) include any other suitable source of light. In general, a source of light would be considered suitable if it is capable of transmitting enough light to the blood separation chamber 34 that the light detector 160 will be able to detect an image thereof.

To allow the monitoring system 156 to directly monitor the blood separation chamber 34, one section or region of the centrifuge bowl 54 may be transparent to the light emitted by the light source 158. In the illustrated embodiment, the region comprises a window 162 cut out or defined in the bowl 54. The remainder of the bowl 54 that lies in the path of the monitoring system 156 may be comprised of an opaque or light absorbing material.

Figure 15:
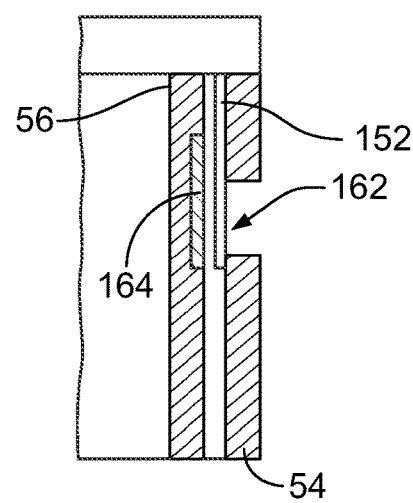
FIG. 15 is a side section view of the centrifuge bowl and spool of FIGS. 3 and 4.

At least a portion of the window 162 may coincide with the region in which the bowl 54 overlies the interface ramp 152 (FIG. 15). In such an embodiment, the interface ramp 152 may be made of a light transmissive material such that, when the window 162 is in the field of view of the monitoring system 156, light from the light source 158 will pass through the window 162 of the bowl 54 and the ramp 152.

The spool 56 may carry a light reflective material 164 (FIG. 15) behind the interface ramp 152 to enhance its reflective properties. The light reflective material 164 of the spool 56 reflects incoming light received from the light source 158 out through the window 162 of the bowl 54, where it is detected by the light detector 160 to form an image. The monitoring system 156 may include a focusing lens and/or reflectors with which light returning from the centrifuge 52 interacts prior to receipt by the light detector 160. The light detector 160 may be variously configured without departing from the scope of the present disclosure, and the monitoring system 156 is not limited to one light detector 160, but may include a plurality of light detectors.

The monitoring system 156 also includes a controller, which may be the central controller of the separation device 10 or may be a separate component that interacts with the central controller. The controller receives data from the light detector 160 and uses the data to determine any of a number of characteristics of the flow circuit 12 within the centrifuge 52, including the location of the interface 150 on the ramp 152. One example of a suitable optical monitoring system is described in greater detail in U.S. Pat. No. 9,594,020, which is hereby incorporated herein by reference.

In one embodiment, the location of the interface 150 on the ramp 152 is determined by the controller based on a change in the amount of light that is transmitted through the RBC and plasma layers 142 and 148. For example, the light source 158 may be configured to emit a light that is more readily transmitted by plasma than by red blood cells, such as red visible light, which is substantially absorbed by red blood cells. The plasma layer 148 and the RBC layer 142 each occupy a certain portion of the ramp 152, with the light detector 160 receiving different amounts of light depending on whether the light travels through the plasma layer 148 on the ramp 152 or the RBC layer 142 on the ramp 152. The percentage of the ramp 152 occupied by each layer is related to the location of the interface 150 in the chamber 34. Thus, by measuring the amount of time that the voltage output or signal from the light detector 160 is relatively high (corresponding to the time during which the light is passing through only the plasma layer 148 on the ramp 152), the controller may determine the location of the interface 150 and take steps to correct the location of the interface 150, if necessary.

More particularly, the light detector 160 will receive no light from the light source 158 when the window 162 (and light reflective material 164) is out of alignment with the initial path of the light from the light source 158, such that the output voltage of the light detector 160 (i.e., the signal transmitted from the light detector 160 to the controller) at this time is in a low- or zero-state.

When the window 162 is first rotated into the path of light from the stationary light source 158, the light detector 160 may begin receiving reflected light. The amount of light received by the light detector 160 depends upon the fluid on the ramp 152 encountered by the light (i.e., the fluid in the first stage 62 of the chamber 34 between the ramp 152 and the spool 56 that the light must traverse before being directed to the light detector 160). As described above and shown in FIG. 10-12, the plasma layer 148 occupies a certain percentage of the first stage 62 adjacent to the spool 56 or low-G wall 146, while the RBC layer 142 occupies a certain percentage of the first stage 62 adjacent to the bowl 54 or high-G wall 144 (with the interface 150 positioned at the transition between the two separated blood component layers). The ramp 152 is closest to the spool 56 or low-G wall 146 at a first end, while being farther spaced from the spool 56 or low-G wall 146 at a second end. At and adjacent to its first end (the left end in the orientation of FIGS. 10-12), the ramp 152 will display only the fluid positioned closest to the spool 56 or low-G wall 146 (i.e., the plasma layer 148), while the ramp 152 will display only the fluid positioned closest to the bowl 54 or high-G wall 144 (i.e., the RBC layer 142) at and adjacent to its second end (the right end in the orientation of FIGS. 10-12).

At some point between its ends, the angled ramp 152 will be at a radial position where it will display the transition between the plasma layer 148 and the RBC layer 142 (i.e., the interface 150). Hence, the location of the interface 150 on the ramp 152 is dependent upon the percentage of the width of the ramp 152 that displays the plasma layer 148 (which is indicative of the percentage of the first stage 62 of the chamber 34 occupied by the plasma layer 148) and the percentage of the width of the ramp 152 that displays the RBC layer 142 (which is indicative of the percentage of the first stage 62 of the chamber 34 occupied by the RBC layer 142).

As the ramp 152 is rotated into the path of the light from the light source 158, the light will first encounter the portion of the ramp 152 that is positioned closest to the low-G wall 146 (i.e., the left end in the orientation of FIGS. 10-12). As described above, the plasma layer 148 will be positioned adjacent to the low-G wall 146 as it separates from the RBC layer 142, such that the fluid displayed on this radially innermost section of the ramp 152 (i.e., the fluid present in the first stage 62 between the ramp 152 and the low-G wall 146) will be the plasma layer 148. The light is substantially transmitted through the plasma layer 148 to the light reflective material 164 (FIG. 15), which redirects the light to the light detector 160. This causes the voltage output of the light detector 160 (i.e., the signal transmitted from the light detector 160 to the controller) to increase to a non-zero value or state.

Further rotation of the ramp 152 through the path of light from the light source 158 exposes the light to portions of the ramp 152 that are increasingly spaced from the low-G wall 146 or spool 56 (i.e., the light travels through portions of the first stage 62 that are less restricted by the ramp 152 as the ramp 152 is rotated through the path of the light). Up until the time that the interface 150 on the ramp 152 is rotated into the path of the light, the only fluid in the first stage 62 that the light will have passed through will be the plasma layer 148, such that a generally uniform level of light reaches the light detector 160. Accordingly, the voltage output of the light detector 160 will be generally uniform (at an elevated level) the whole time that the ramp 152 passes through the path of the light before being exposed to the interface 150.

Just after the interface 150 has been rotated into the path of light from the light source 158, the light will begin to encounter the RBC layer 142 in the first stage 62. As described above, the RBC layer 142 will be positioned adjacent to the high-G wall 144 or bowl 54 as it separates from the plasma layer 148, such that the RBC layer 142 will not be displayed on the ramp 152 until the ramp 152 is spaced a greater distance away from the low-G wall 146 (i.e., toward the second or right end of the ramp 152 in the orientation of FIGS. 10-12). Less light is transmitted through the RBC layer 142 than through the plasma layer 148 (which may include all or substantially all of the light being absorbed by the RBC layer 142), such that the amount of light that reaches the light detector 160 will decrease compared to the amount of light that reaches the light detector 160 while traveling through only the plasma layer 148 in the first stage 62.

When receiving less light, the voltage output or signal from the light detector 160 will decrease to a lower level than when the light was passing through only the plasma layer 148 in the first stage 62. When the light encounters the RBC layer 142 in the first stage 62, the light detector 160 may be generating a signal or voltage output that is approximately equal to its zero-state (such as when the light detector 160 is receiving no light due to the window 160 being out of alignment with the monitoring system 156) or a signal or voltage output that is some degree less than the magnitude of the signal or voltage output generated while the light encounters only the plasma layer 148 in the first stage 62. The controller may be programmed and/or configured to recognize this lower level signal as representing the presence of the RBC layer 142 on the ramp 152 and treat this lower level signal as the end point of the elevated signal generated by the light detector 160 while light passes through only the plasma layer 148 in the first stage 62.

Thus, the pulse width of the elevated signal from the light detector 160 to the controller (i.e., the time during which light is traversing only the plasma layer 148 in the first stage 62) is determined by the percentages of the ramp 152 that are occupied by the plasma layer 148 and the RBC layer 142. Accordingly, a greater pulse width of the signal from the light detector 160 to the controller is associated with the plasma layer 148 occupying a larger portion of the ramp 152 (as shown in FIG. 12) and will be indicative of a thinner RBC layer 142 on the ramp 152 (and in the first stage 62). Conversely, a signal from the light detector 160 to the controller having a narrower pulse width is associated with the plasma layer 148 occupying a smaller portion of the ramp 152 (as shown in FIG. 11) and will be indicative of a thicker RBC layer 142 on the ramp 152 (and in the first stage 62).

The controller may compare the pulse width of the signal to the expected pulse width when the interface 150 is at the proper position on the ramp 152 to determine the location of the various separated blood components within the first stage 62. The difference between the expected interface position and the calculated interface position may be referred to as the error signal.

When the control value is expressed in terms of a targeted red blood cell percentage value, a negative error signal indicates that the RBC layer 142 on the ramp 152 is too large (as FIG. 11 shows). The controller generates a signal to adjust an operational parameter accordingly, such as by reducing the rate at which the plasma layer 148 is removed through the outlet port 68 under action of a pump 92 of the separation device 10. This effectively increases the amount of the plasma layer 148 in the first stage 62, thus causing the interface 150 to move toward the desired control position (as FIG. 10 shows), where the error signal is zero.

A positive error signal indicates that the RBC layer 142 on the ramp 152 is too small (as FIG. 12 shows). The controller generates a signal to adjust an operational parameter accordingly, such as by increasing the rate at which the plasma layer 148 is removed through the outlet port 68 under action of a pump 92 of the separation device 10. This effectively decreases the amount of the plasma layer 148 in the first stage 62, thus causing the interface 150 to move toward the desired control position (FIG. 10), where the error signal is zero.

It should be understood that this system for controlling the location of the interface 150 is merely exemplary and that differently configured and/or functioning systems may be employed without departing from the scope of the present disclosure.

The ability of the controller to determine the location of the interface 150 and any other characteristics of the flow circuit 12 depends on a clear field of vision between the monitoring system 156 and the window 162. When the umbilicus 48 and/or yoke 58 passes between the monitoring system 156 and the window 162, it prevents light from being transmitted from the monitoring system 156 to the centrifuge 52 and from being reflected back from the centrifuge 52 to the monitoring system 156. Additionally, depending on the nature of the light from the light source 158 and the configuration of the umbilicus 48 and/or yoke 58, it is possible for the umbilicus 48 and/or yoke 58 to reflect light back to the light detector 160. Thus, the presence of the umbilicus 48 and/or yoke 58 between the monitoring system 156 and the window 162 can prevent the controller from receiving a reliable pulse width from the light detector 160, which prevents the controller from determining the location of the interface 150 on the ramp 152.

According to one aspect of an approach to preventing the umbilicus 48 from interfering with optical monitoring of the flow circuit 12 within the centrifuge 52, the portion of the umbilicus 48 positioned to pass through the field of vision of the monitoring system 156 may be rendered less reflective (e.g., by applying black paint and/or a matte black tape or finish) to decrease the tendency of the umbilicus 48 to reflect light back to the light detector 160. The width of the umbilicus 48 may be comparable to a possible pulse width of light reflected back to the light detector 160 from the centrifuge 52, so rendering the umbilicus 48 non-reflective or at least less reflective prevents the controller from receiving a signal caused by light reflected by the umbilicus 48 that could be misinterpreted as light reflected by the centrifuge 52.

The yoke 58 is designed such that, for every complete rotation of the yoke 58, at least one out of every two rotations of the ramp window 162 into alignment with the monitoring system 156 may be viewed completely and without obstruction. The controller is programmed and/or configured to determine which signals correspond to light reflected by the centrifuge 52 through the window 162 and select the most complete (i.e., the widest) for use in determining a characteristic of the chamber 34 (e.g., interface location). A suitable yoke 162 is shown in greater detail in FIGS. 16 and 17.

The yoke 58 includes first and second support arms 166 and 168, which are shown as being generally diametrically opposed, with the centrifuge bowl 54 positioned therebetween. One of the support arms (illustrated as second support arm 168) defines an opening or aperture or window 170 therethrough. The yoke window 170 is configured to provide a sight line through the support arm 168 to allow the monitoring system 156 to view and monitor the ramp 152. Accordingly, the yoke window 170 is preferably significantly larger than the ramp 152 to maximize the visibility of the ramp 152 through the support arm 168, with a height (the vertical dimension in the orientation of FIG. 16) that is greater than the height of the ramp 152 (shown in FIG. 16 as a pair of broken lines 172 to represent the multiple possible positions of the ramp 152 as the centrifuge bowl 54 is rotated) and a width or angular extent (best shown in FIG. 17) that is greater than the width or angular extent of the ramp 152. Preferably, the yoke window 170 is positioned with the ramp 152 centered along the height of the yoke window 170 (i.e., with the vertical center of the ramp 152 being at the same elevation as the vertical center of the yoke window 170 in the orientation of FIG. 16), but it is also within the scope of the present disclosure for the ramp 152 to be closer to the top or bottom of the yoke window 170.

Figure 17:
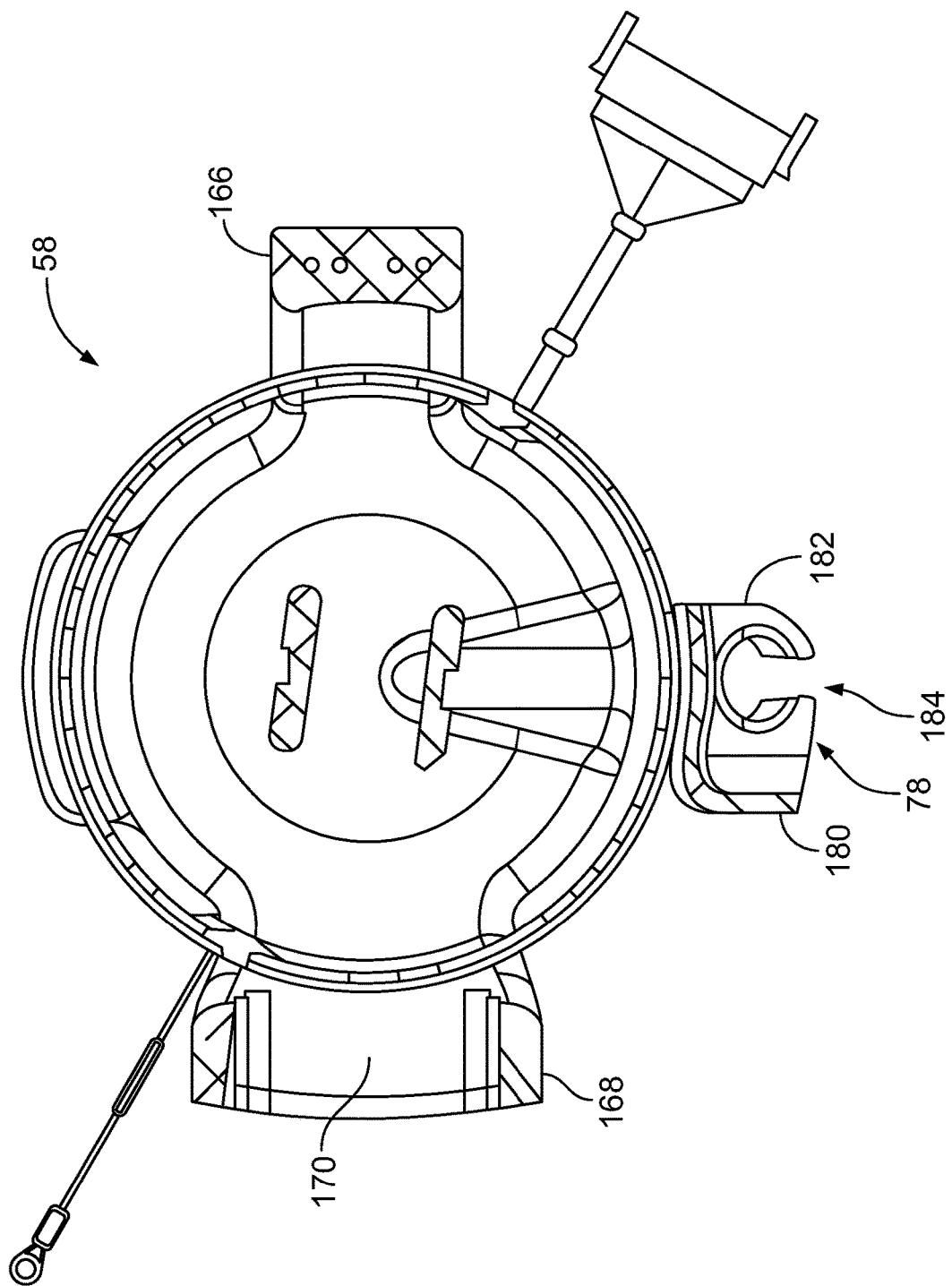
FIG. 17 is a cross-sectional plan view of the yoke of FIG. 16.

Increasing the width or angular extent of the yoke window 170 increases the visibility of the ramp 152 by the monitoring system 156. As best shown in FIG. 17, the yoke window 170 preferably has a width or angular extent equal to or greater than that of the opposing support arm 166 at the same elevation, with the other support arm 166 being diametrically opposed to the yoke window 170. By such a configuration, there is never one visual obstruction or obstacle (e.g., one of the support arms 166, 168) positioned 180° from another visual obstruction or obstacle (e.g., the other support arm).

The illustrated configuration may be preferred because of the fact that the yoke 58 rotates at one half the average speed of the centrifuge bowl 54, as described above in greater detail. In such a rotational relationship, a 180° rotation of the yoke 58 will result in a 360° rotation of the centrifuge bowl 54 on average. Thus, the ramp 152 will be at the same approximate position (e.g., in position to be viewed by the monitoring system 156) upon each 180° rotation of the yoke 58. Accordingly, if the yoke is provided with visual obstructions or obstacles positioned 180° apart, then it may be that the view of the ramp 152 will be obstructed during consecutive 360° rotations of the centrifuge bowl 54. In contrast, if the yoke is provided so as to eliminate any obstructions positioned 180° apart (as in the embodiment of FIGS. 16 and 17), then even if the view of the ramp 152 is obstructed at one time, the view of the ramp 152 by the monitoring system 156 will be clear during the next 360° rotation of the centrifuge bowl 54.

As noted above, the controller is programmed and/or configured to accommodate the potential for partially obscured ramp-induced signals by only capturing the longest pulse in a given 100 ms interval or timing cycle. At 1,640 RPM for the yoke 58, the centrifuge 52 is spinning at approximately 55 Hz, such that about 5½ ramp-induced signals should be seen per timing cycle and at least half of these will be unobstructed views of the ramp window 162. This design ensures that at least two unobscured, full signals will be viewed and measured by the monitoring system 156 and associated controller per timing cycle.

The portions of the yoke 58, including the umbilicus holder 78, positioned to pass through the field of vision of the monitoring system 156 are configured to be relatively reflective. In one embodiment, these portions of the yoke 58 are sufficiently reflective so as to reflect light from the light source 158 to the light detector 160 at a level that is comparable to the brightness of light reflected through the ramp window 162 by the centrifuge 52. Thus, the signals received by the controller caused by light reflected by the yoke 58 are comparable in magnitude or voltage to the signals received when light is reflected back to the light detector 160 through the ramp window 162 by the centrifuge 52.

Figure 18:
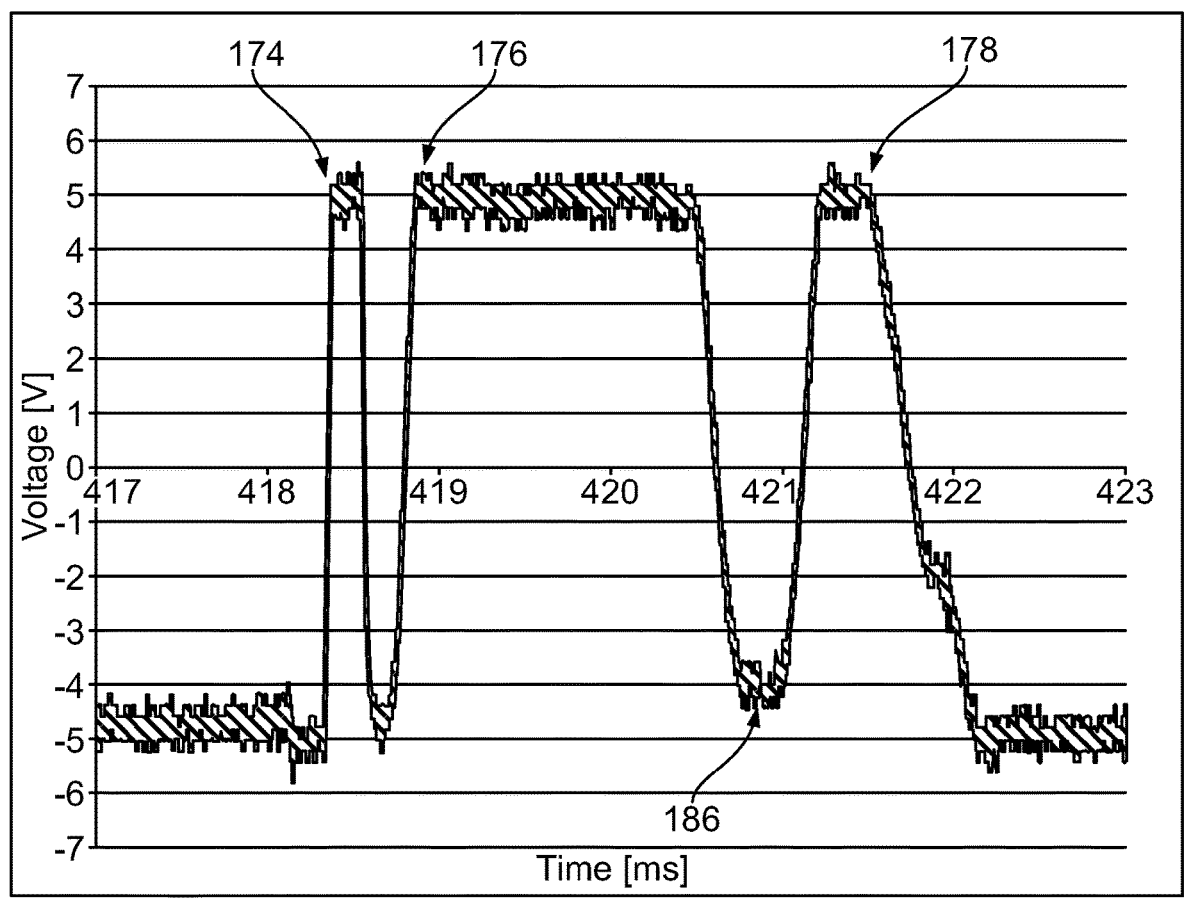
FIG. 18 is a chart showing signals received by a controller in monitoring the centrifuge.

FIG. 18 shows the signals received by the controller during a portion of a timing cycle. It should be understood that FIG. 18 represents an exemplary portion of a timing cycle and that the signals received by the controller over the course of an entire timing cycle may differ from the portion represented in FIG. 18. Additionally, the signals received by the controller during one timing cycle may differ from the signals received by the controller during another timing cycle. However, as the yoke 58 rotates at a uniform, predictable rate, the signals received by the controller due to a portion of the yoke 58 being aligned with the monitoring system 156 should be generally predictable and periodic. The controller may be programmed and/or configured to use this predictability to discern ramp-induced signals from yoke-induced signals.

In the time frame represented by FIG. 18, three high-voltage signals 174, 176, and 178 are received by the controller. As the yoke 58 and centrifuge 52 rotate (in a clockwise direction in the orientation of FIG. 17), light reflected back to the light detector 160 through the ramp window 162 by the centrifuge 52 will generate a high-voltage signal if the yoke 58 is not aligned with the monitoring system 156 at the same time as the ramp window 162. In the time frame represented by FIG. 18, the first high-voltage signal 174 is attributable to light reflected back to the light detector 160 through the ramp window 162 by the centrifuge 52. As described above in greater detail, the width of the signal depends upon the percentage of the ramp 152 occupied by the plasma layer 148, up to a width that corresponds to the width of the entire ramp window 162, which may occur during a pre-processing calibration phase during which a light-transmissive fluid (e.g., saline) occupies the entire ramp 152.

When the ramp window 162 rotates out of alignment with the monitoring system 156 and the centrifuge bowl 54 rotates into alignment with the monitoring system 156, the voltage received by the controller decreases, as shown in FIG. 18 by a decrease in the magnitude of the signal immediately following the first high-voltage signal 174 and preceding the second high-voltage signal 176.

In the time frame represented by FIG. 18, a portion of the yoke 58 rotates into alignment with the monitoring system 156 next. In particular, the leading portion 180 of the umbilicus holder 78 (i.e, the portion of the umbilicus holder 78 that rotates into alignment with the monitoring system 156 before a trailing portion 182) rotates into alignment with the monitoring system 156. As described above, the portions of the yoke 58 configured to pass into the field of vision of the monitoring system 156 (including the leading portion 180 of the umbilicus holder 78) are relatively reflective, so the leading portion 180 reflects enough light back to the light detector 160 so as to cause a high-voltage signal 176.

As can be seen in FIG. 18, the high-voltage signal 176 generated by light reflected from the leading portion 180 of the umbilicus holder 78 is much wider or longer than the ramp-induced high-voltage signal 174 (and than the greatest possible pulse width of a ramp-induced high-voltage signal). The controller is programmed and/or configured to determine that a high-voltage signal with a pulse width that is greater than the maximum pulse width caused by an instance of light reflected through the ramp window 156 by the centrifuge 52 without obstruction is caused by alignment of a portion of the yoke 58 with the monitoring system 156.

As shown in FIG. 17, the umbilicus holder 78 includes a cavity 184, which separates the leading portion 180 from the trailing portion 182. This is the portion of the umbilicus holder 78 that receives the midsection of the umbilicus 48. The umbilicus 48 is relatively non-reflective or at least less reflective than the yoke 58 (including the umbilicus holder 78), such that rotating the cavity 184 and umbilicus 48 into alignment with the monitoring system 156 will cause the voltage received by the controller to decrease. This is represented in FIG. 18 at 186, which is a decrease in the magnitude of the signal immediately following the second high-voltage signal 176 and preceding the third high-voltage signal 178.

Next, the trailing portion 182 of the umbilicus holder 78 rotates into alignment with the monitoring system 156. As described above, the portions of the yoke 58 configured to pass into the field of vision of the monitoring system 156 (including the trailing portion 182 of the umbilicus holder 78) are relatively reflective, so the trailing portion 182 reflects enough light back to the light detector 160 so as to cause a high-voltage signal 178.

In contrast to the high-voltage signal 176 generated by light reflected from the leading portion 180 of the umbilicus holder 78, the signal 178 generated by light reflected from the trailing portion 182 of the umbilicus holder 78 is comparable to the pulse width of the ramp-induced high-voltage signal 174 (while being less than the greatest possible pulse width of a ramp-induced high-voltage signal). According to one embodiment, the controller may be programmed and/or configured to determine that a high-voltage signal (such as signal 178) immediately following a high-voltage signal with a pulse width that is greater than the maximum pulse width caused by an instance of light reflected through the ramp window 156 by the centrifuge 52 without obstruction (such as signal 176) is caused by alignment of a portion of the yoke 58 with the monitoring system 156. Conversely, the controller may be programmed and/or configured to determine that a high-voltage signal having a pulse width no greater than the maximum possible for a ramp-induced signal (such as signal 174) not immediately following a high-voltage signal with a pulse width that is greater than the maximum pulse width caused by an instance of light reflected through the ramp window 156 by the centrifuge 52 without obstruction (such as signal 176) is a ramp-induced signal.

The controller may additionally or alternatively be programmed and/or configured to enforce a minimum gap or time between consecutive high-voltage signals. The controller compares the time between consecutive high-voltage signals and, if the time is less than the predetermined time (which may vary without departing from the scope of the present disclosure), then both signals may be discarded. This may result in a ramp-induced signal, such as signal 174 in FIG. 18, being discarded due to its proximity to another signal, but this may be preferred to ensure that the ramp-induced signal is complete and unobstructed. As described above, each timing signal will include at least two unobstructed, ramp-induced high-voltage signals, so even discarding one of them leaves another unobstructed, ramp-induced high-voltage signal for monitoring functions.

When the controller has determined which signals are ramp-induced and which are yoke-induced during a particular timing cycle, including discarding any consecutive signals not separated by the minimum gap (if the controller is so programmed and/or configured), it may compare the various ramp-induced signals observed during a particular timing cycle. The controller selects the ramp-induced signal having the greatest pulse width during the timing cycle to determine a characteristic of the disposable flow circuit 12, such as the interface position on the ramp 152.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood processing system, comprising:
a centrifuge configured for rotation about a rotational axis, wherein the centrifuge includes a radially facing window and is configured to receive at least a portion of a disposable flow circuit including an umbilicus;
a yoke configured to orbit a midsection of the umbilicus around the rotational axis at a uniform first speed so as to cause the centrifuge to rotate at a non-uniform second speed with an average speed that is approximately double the first speed;
a monitoring system positioned radially of the centrifuge, configured to directly monitor the disposable flow circuit through the window, and comprising a light source, a light detector, and a controller, wherein
the light source is oriented to emit a light passing through the window when the window is rotated into alignment with the monitoring system,
the light detector is oriented to receive a light reflected through the window by the centrifuge when the window is aligned with the monitoring system,
the controller is configured to receive a plurality of signals from the light detector when the light detector receives reflected light during a timing cycle,
a portion of the yoke and the midsection of the umbilicus are rotatable into and out of position between the monitoring system and the window when the window is aligned with the monitoring system,
said portion of the yoke is configured to receive light from the light source when said portion of the yoke is aligned with the monitoring system and to reflect said light to the light detector, and
the controller is configured to
determine which of the signals from the light detector during the timing cycle is caused by light reflected through the window by the centrifuge or by light reflected by said portion of the yoke,
compare a pulse width of each of the signals caused by light reflected through the window by the centrifuge during the timing cycle, and
use the signal caused by light reflected through the window by the centrifuge having the greatest pulse width during the timing cycle to determine a characteristic of the disposable flow circuit.

2. The blood processing system of claim 1, wherein the timing cycle is selected such that the window is expected to be in alignment with the monitoring system at least five times during the timing cycle.

3. The blood processing system of claim 2, wherein the yoke and the umbilicus are configured such that the light detector is expected to receive at least two instances of unobstructed reflected light from the centrifuge through the window during the timing cycle.

4. The blood processing system of claim 1, wherein the timing cycle is approximately 100 milliseconds.

5. The blood processing system of claim 1, wherein the controller is configured to determine that a signal from the light detector is caused by light reflected by said portion of the yoke when the pulse width of the signal is greater than the maximum pulse width caused by an instance of light reflected through the window by the centrifuge and received by the light detector without obstruction by said portion of the yoke and/or the umbilicus.

6. The blood processing system of claim 1, wherein the controller is configured to determine that a signal having a pulse width that is no greater than the maximum pulse width caused by an instance of light reflected through the window by the centrifuge and received by the light detector without obstruction by said portion of the yoke and/or umbilicus is caused by light reflected by said portion of the yoke when the signal immediately follows a signal having a pulse width greater than the maximum pulse width caused by an instance of light reflected through the window by the centrifuge and received by the light detector without obstruction by said portion of the yoke and/or the umbilicus.

7. The blood processing system of claim 1, wherein the controller is configured to determine that a signal having a pulse width that is no greater than the maximum pulse width caused by an instance of light reflected through the window by the centrifuge and received by the light detector without obstruction by said portion of the yoke and/or the umbilicus is caused by light reflected through the window by the centrifuge when the signal does not immediately follow a signal having a pulse width greater than the maximum pulse width caused by an instance of light reflected through the window by the centrifuge and received by the light detector without obstruction by said portion of the yoke and/or the umbilicus.

8. The blood processing system of claim 1, wherein the controller is configured to compare the time between consecutive signals to a predetermined minimum time and, if the time between two consecutive signals is less than the predetermined minimum time, prevent the two consecutive signals from being used to determine said characteristic of the disposable flow circuit.

9. The blood processing system of claim 1, wherein said characteristic of the disposable flow circuit is the position of an interface between separated blood components within the disposable flow circuit.

10. The blood processing system of claim 9, wherein the controller is configured to compare the position of the interface to an expected position and, if the position is different from the expected position, adjust an operational parameter to move the interface toward the expected position.

11. A method of determining a characteristic of a disposable flow circuit at least partially positioned within a centrifuge of the type configured for rotation about a rotational axis and including a radially facing window, the method comprising:
  rotating a yoke about the rotational axis so as to orbit a midsection of an umbilicus of the disposable flow circuit around the rotational axis at a uniform first speed, thereby causing the centrifuge to rotate at a non-uniform second speed with an average speed that is approximately double the first speed;
  emitting a light from a radial position with respect to the centrifuge, wherein the light
    passes through the window and is reflected through the window by the centrifuge when
      the window is rotated into alignment with a light source and
      the yoke and umbilicus are not positioned between the light source and the window, and
    is reflected by a portion of the yoke when said portion of the yoke is positioned between the light source and the centrifuge;
  receiving reflected light a plurality of times during a timing period;
  converting each instance of reflected light that is received into a signal;
  determining which of the signals is caused by light reflected through the window by the centrifuge or by light reflected by said portion of the yoke;
  comparing a pulse width of each of the signals caused by light reflected through the window by the centrifuge during the timing cycle; and
  using the signal caused by light reflected through the window by the centrifuge having the greatest pulse width during the timing cycle to determine a characteristic of the disposable flow circuit.

12. The method of claim 11, wherein the timing cycle is selected such that the window is expected to be in alignment with the light source at least five times during the timing cycle.

13. The method of claim 12, wherein the yoke and the umbilicus are configured such that at least two instances of unobstructed reflected light from the centrifuge through the window are expected to be received during the timing cycle.

14. The method of claim 11, wherein the timing cycle is approximately 100 milliseconds.

15. The method of claim 11, wherein said determining which of the signals is caused by light reflected through the window by the centrifuge or by light reflected by said portion of the yoke includes determining that a signal is caused by light reflected by said portion of the yoke when the pulse width of the signal is greater than the maximum pulse width caused by an instance of light reflected through the window by the centrifuge without obstruction by said portion of the yoke and/or the umbilicus.

16. The method of claim 11, wherein said determining which of the signals is caused by light reflected through the window by the centrifuge or by light reflected by said portion of the yoke includes determining that a signal having a pulse width that is no greater than the maximum pulse width caused by an instance of light reflected through the window by the centrifuge without obstruction by said portion of the yoke and/or umbilicus is caused by light reflected by said portion of the yoke when the signal immediately follows a signal having a pulse width greater than the maximum pulse width caused by an instance of light reflected through the window by the centrifuge without obstruction by said portion of the yoke and/or the umbilicus.

17. The method of claim 11, wherein said determining which of the signals is caused by light reflected through the window by the centrifuge or by light reflected by said portion of the yoke includes determining that a signal having a pulse width that is no greater than the maximum pulse width caused by an instance of light reflected through the window by the centrifuge without obstruction by said portion of the yoke and/or the umbilicus is caused by light reflected through the window by the centrifuge when the signal does not immediately follow a signal having a pulse width greater than the maximum pulse width caused by an instance of light reflected through the window by the centrifuge without obstruction by said portion of the yoke and/or the umbilicus.

18. The method of claim 11, further comprising comparing the time between consecutive signals to a predetermined minimum time and, if the time between two consecutive signals is less than the predetermined minimum time, preventing the two consecutive signals from being used to determine said characteristic of the disposable flow circuit.

19. The method of claim 11, wherein said characteristic of the disposable flow circuit is the position of an interface between separated blood components within the disposable flow circuit.

20. The method of claim 19, further comprising comparing the position of the interface to an expected position and, if the position is different from the expected position, adjusting an operational parameter to move the interface toward the expected position.

* * * * *